United States Patent
Geibel et al.

(10) Patent No.: US 8,486,381 B2
(45) Date of Patent: *Jul. 16, 2013

(54) METHODS OF MODULATING INTESTINAL FLUID BALANCE

(75) Inventors: John Peter Geibel, Branford, CT (US); Steven Charles Hebert, Woodbridge, CT (US); David Martin, Camarillo, CA (US); Deborah A. Russell, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 368 days.

This patent is subject to a terminal disclaimer.

(21) Appl. No.: 11/511,036

(22) Filed: Aug. 28, 2006

(65) Prior Publication Data

US 2007/0060625 A1    Mar. 15, 2007

Related U.S. Application Data

(60) Provisional application No. 60/789,036, filed on Apr. 4, 2006, provisional application No. 60/713,977, filed on Sep. 2, 2005.

(51) Int. Cl.
    *A61K 31/74*    (2006.01)
(52) U.S. Cl.
    USPC ........ 424/78.01; 514/357; 514/522; 514/602; 514/408; 514/649; 514/567; 514/597; 514/236.8; 514/327; 514/330
(58) Field of Classification Search
    USPC .............. 424/78.1; 514/357, 522, 602, 408, 514/649, 567, 597, 236.8, 327, 330
    See application file for complete search history.

(56) References Cited

U.S. PATENT DOCUMENTS

| | | | |
|---|---|---|---|
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,395,919 B1 | 5/2002 | Bhatnagar et al. | |
| 6,750,255 B2 | 6/2004 | Sakai et al. | |
| 6,849,661 B2 | 2/2005 | Kelly et al. | |
| 6,908,935 B2 | 6/2005 | Kelly et al. | |
| 7,176,322 B2 | 2/2007 | Kelly et al. | |
| 2002/0107406 A1 | 8/2002 | Sakai et al. | |
| 2004/0219232 A1 | 11/2004 | Lipton | |
| 2011/0178133 A1* | 7/2011 | Coulter et al. | 514/341 |

FOREIGN PATENT DOCUMENTS

| | | |
|---|---|---|
| WO | WO93/04373 | 3/1993 |
| WO | WO94/18959 | 9/1994 |
| WO | WO 95/11224 A | 4/1995 |
| WO | WO 96/12697 A | 5/1996 |
| WO | WO97/37967 | 10/1997 |
| WO | WO 98/01417 | 1/1998 |

(Continued)

OTHER PUBLICATIONS

Boron, W. F. et al. "Unique Permeability Barrier of the Apical Surface of Parietal and Chief Cells in Isolated Perfused Gastric Glands," Journal of Experimental Biology, 196:347-360, 1994.

(Continued)

*Primary Examiner* — Savitha Rao
(74) *Attorney, Agent, or Firm* — Olga Mckhovich

(57) ABSTRACT

The present invention relates to methods for treating intestinal fluid balance disorders and modulating intestinal fluid secretion and absorption using calcimimetics and calcilytics.

15 Claims, 17 Drawing Sheets

FOREIGN PATENT DOCUMENTS

| WO | WO99/51569 | 10/1999 |
|---|---|---|
| WO | WO 03/099776 | 12/2003 |
| WO | WO 2005/034928 | 4/2005 |

OTHER PUBLICATIONS

Bovee-Oudenhoven, I. M. J. et al. "Increasing the Intestinal Resistance of Rats to the Invasive Pathogen *Salmonella enteritidis*: Additive Effects of Dietary Lactulose and Calcium," Gut, 40(4):497-504, 1997.

Bovee-Oudenhoven, I. M. J. et al. "Diarrhea Caused by Enterotoxigenic *Escherichia coli* Infection of Humans is Inhibited by Dietary Calcium," Gastroenterology, 125:469-476, 2003.

Brown, E. M. et al. "Cloning and Characterization of an Extracellular $Ca^{2+}$-Sensing Receptor from Bovine Parathyroid," Nature, 366:575-580, 1993.

Chattopadhyay, N. et al. "Identification and Localization of Extracellular $Ca^{2+}$-Sensing Receptor in Rat Intestine," American Journal of Physiology, 274:G122-G130, 1998.

Cheng, S. X. et al. "Expression of Calcium-sensing Receptor in Rat Colonic Epithelium: Evidence for Modulation of Fluid Secretion," American Journal of Physiology—Gastrointestinal and Liver Physiology, 283:G240-G250, 2002.

Cheng, S. X. et al. "Extracellular Polyamines Regulate Fluid Secretion in Rat Colonic Crypts Via the Extracellular Calcium-Sensing Receptor," Gastroenterology 126:148-158, 2004.

Chu, S. W. et al "Bacterial Toxin Interaction with the Developing Intestine," Gastroenterology, 104:916-925, 1993.

Conigrave, A. et al. "L-Amino Acid Sensing by the Extracellular $Ca^{2+}$-Sensing Receptor," PNAS, 97(9):4814-4819, 2000.

Cooke, H. J. "'Enteric Tears': Chloride Secretion and its Neural Regulation," News in Physiological Science, 13:269-274, 1998.

Dauban, P. et al. "$N^1$-Arylsulfonyl-$N^2$-(1-arypethyl-3-phenylpropane-1,2-diamines as Novel Calcimimetics Acting on the Calcium Sensing Receptor," Bioorganic & Medicinal Chemistry Letters, 10:2001-2004, 2000.

Field, M. "Intestinal Ion Transport and the Pathophysiology of Diarrhea," The Journal of Clinical Investigation, 111(7):931-943, 2003.

Gama, L. et al. "$Ca^{2+}$-Sensing Receptors in Intestinal Epithelium," American Journal of Physiology, 273:C1168-C1175, 1997.

Geibel, J. P. et al. "Basolateral Sodium-Coupled Acid-Base Transport Mechanisms of the Rabbit Proximal Tubule," American Journal of Physiology, 257:F790-F797, 1989.

Geibel, J. P. et al. "$Na^+$-Dependent Fluid Absorption in Intact Perfused Rat Colonic Crypts," Gastroenterology, 120:144-150, 2001.

Geibel, J. P. "Secretion and Absorption by Colonic Crypts," Annual Review of Physiology, 67:471-490, 2005.

Geibel, J. et al. "Calcium-Sensing Receptor Abrogates Secretagogue-Induced Increases in Intestinal Net Fluid Secretion by Enhancing Cyclic Nucleotide Destruction," PNAS, 103(25):9390-9397, 2006.

Golin-Bisello, F. et al. "STa and cGMP Stimulate CFTR Translocation to the Surface of Villus Enterocytes in Rat Jejunum and is Regulated by Protein Kinase G," American Journal Physiology of Cell Physiology, 289:C708-C716, 2005.

Günther, T. et al. "Genetic Ablation of Parathyroid Glands Reveals Another Source of Parathyroid Hormone," Nature, 406:199-203, 2000.

Ho, C. et al. "A Mouse Model of Human Familial Hypocalciuric Hypercalcemia and Neonatal Severe Hyperparathyroidism," Nature Genetics, 11:389-394, 1995.

Kunzelmann, K. et al. "Electrolyte Transport in the Mammalian Colon: Mechanisms and Implications for Disease," Physiological Reviews, 82:245-289, 2002.

Lucas, M. L. et al. "A Reconsideration of the Evidence for *Escherichia coli* STa (Heat Stable) Enterotoxin-Driven Fluid Secretion: A New View of STa Action and a New Paradigm for Fluid Absorption," Journal of Applied Microbiology, 90: 7-26, 2001.

Ruat, M. et al. "Cloned and Expressed Rat $Ca^{2+}$-Sensing Receptor," The Journal of Biological Chemistry, 271(11):5972-5975, 1996.

Singh, S. K. et al. "An Apical Permeability Barrier to $NH_3/NH_4^+$ in Isolated, Perfused Colonic Crypts," Proceedings of the National Academy of Sciences, 92:11573-11577, 1995.

Tu, Q. et al. "Rescue of the Skeletal Phenotype in *CasR*-Deficient Mice by Transfer onto the *Gcm2* Null Background," 111(7):1029-1037, 2003.

Watanabe, S. et al. "Developmental Regulation of Epithelial Sodium Channel Subunit mRNA Expression in Rat Colon and Lung," American Journal of Physiology, 275:G1227-G1235, 1998.

Yamaguchi, T. et al. "G Protein-Coupled Extracellular $Ca^{2+}$ ($Ca^{2+}_o$)-Sensing Receptor (CaR): Roles in Cell Signaling and Control of Diverse Cellular Functions," Advances in Pharmacology, 47:209-253, 2000.

\* cited by examiner

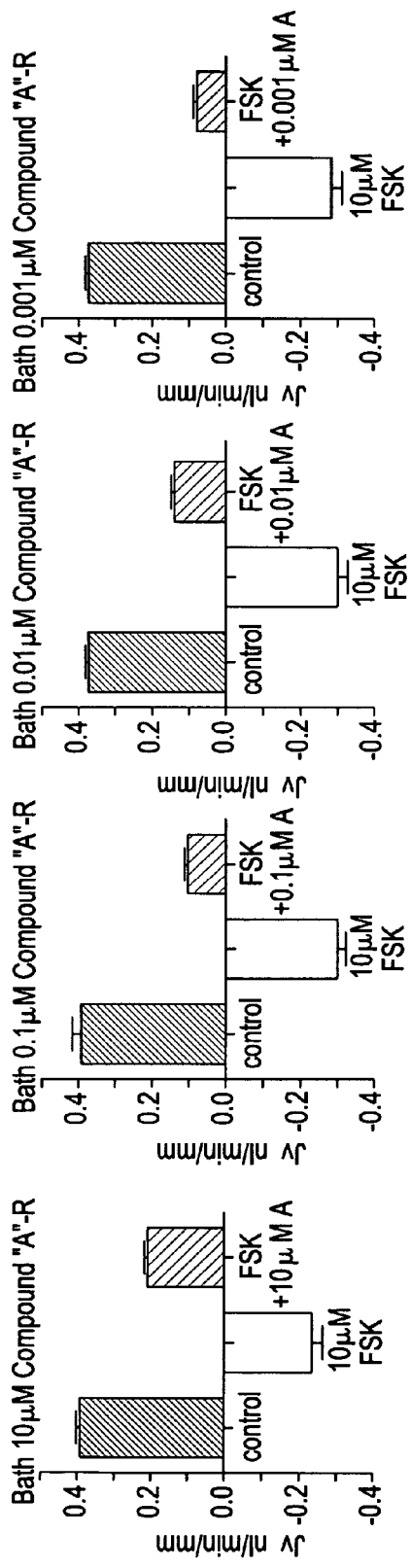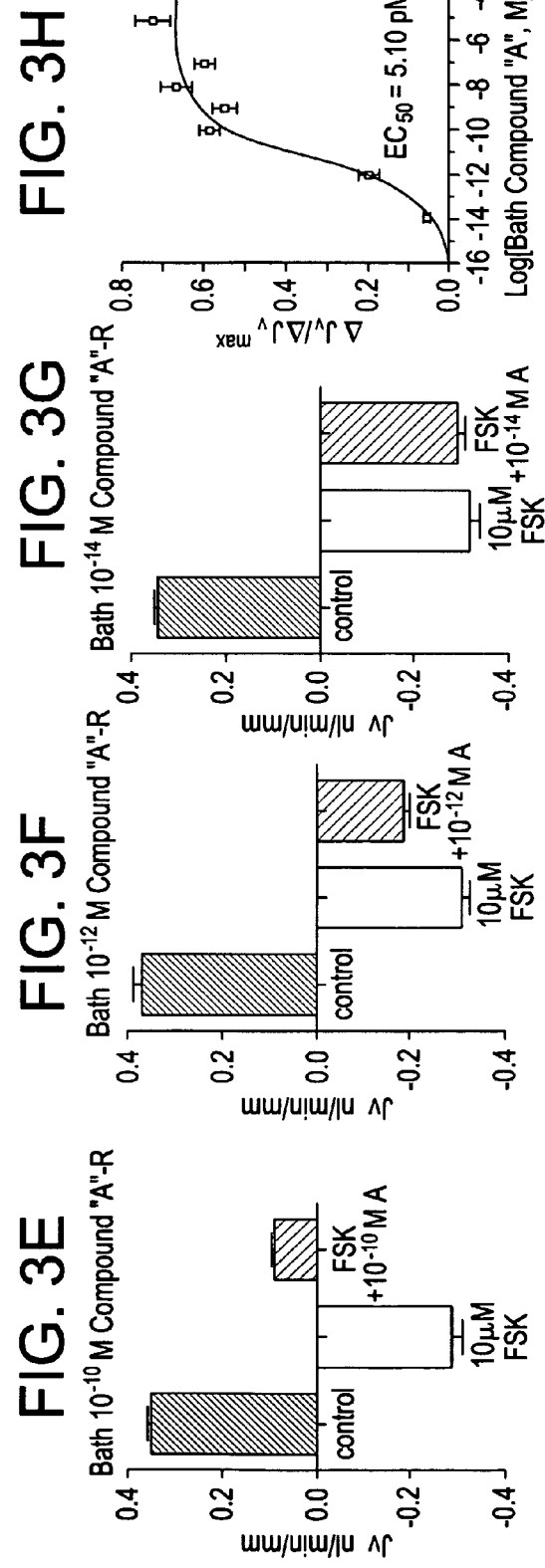

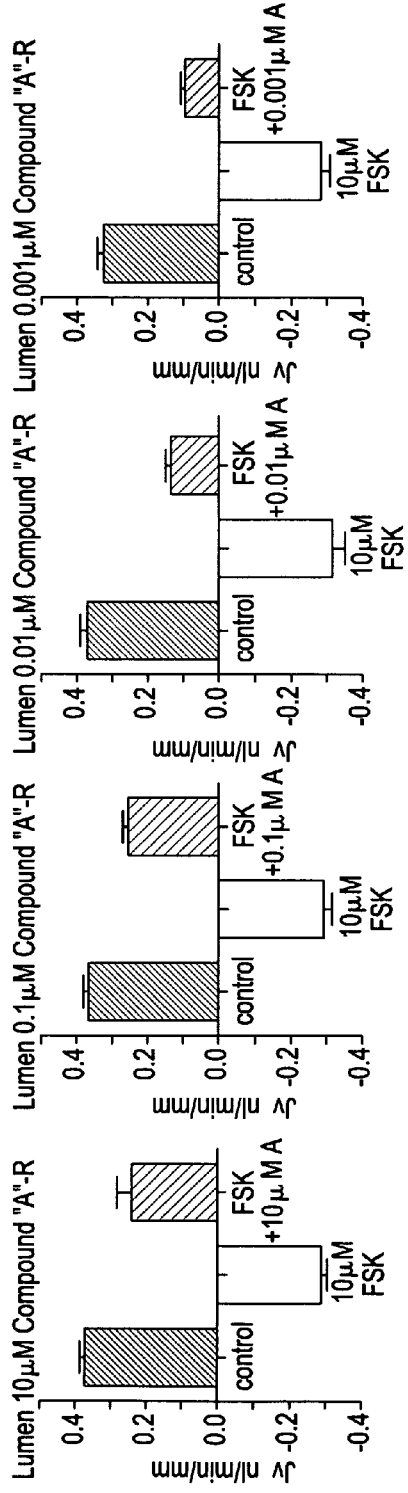
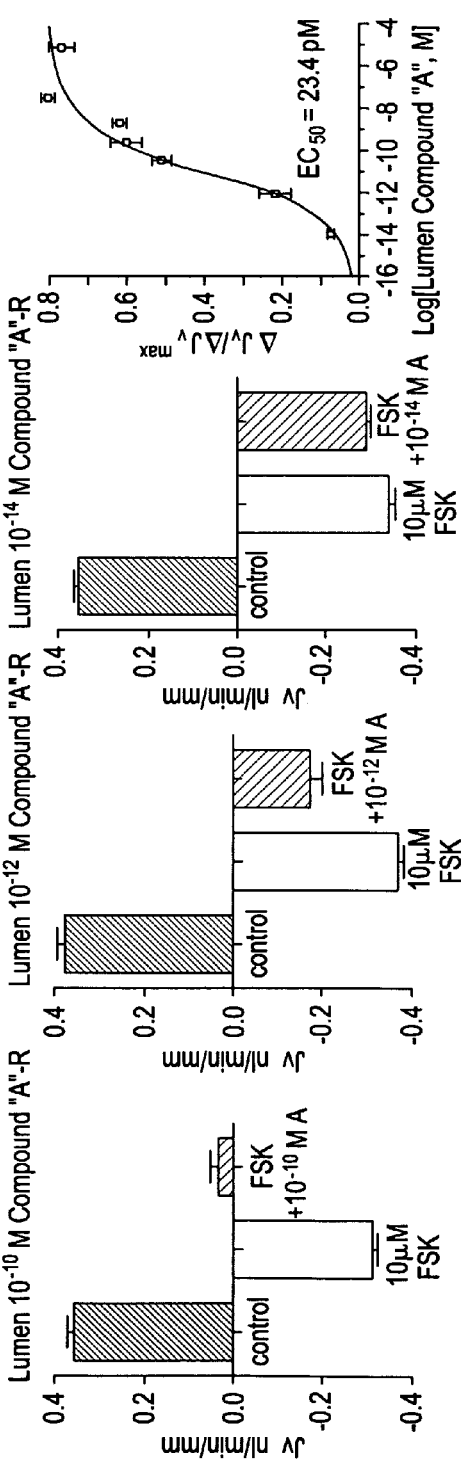
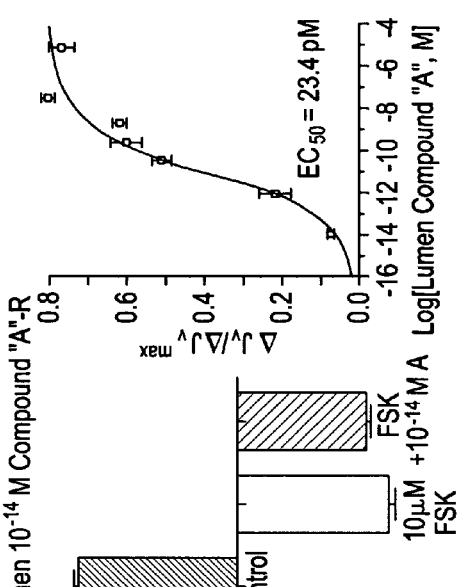

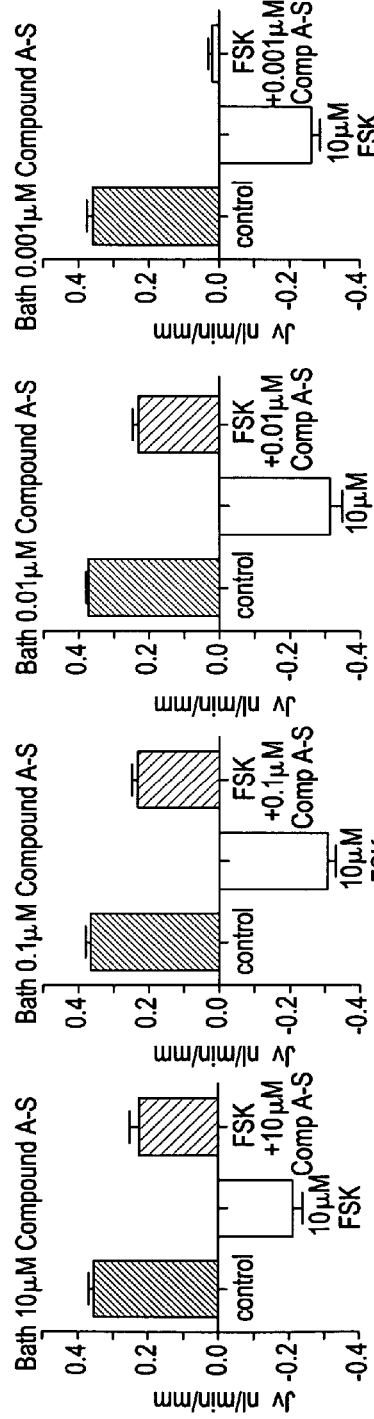
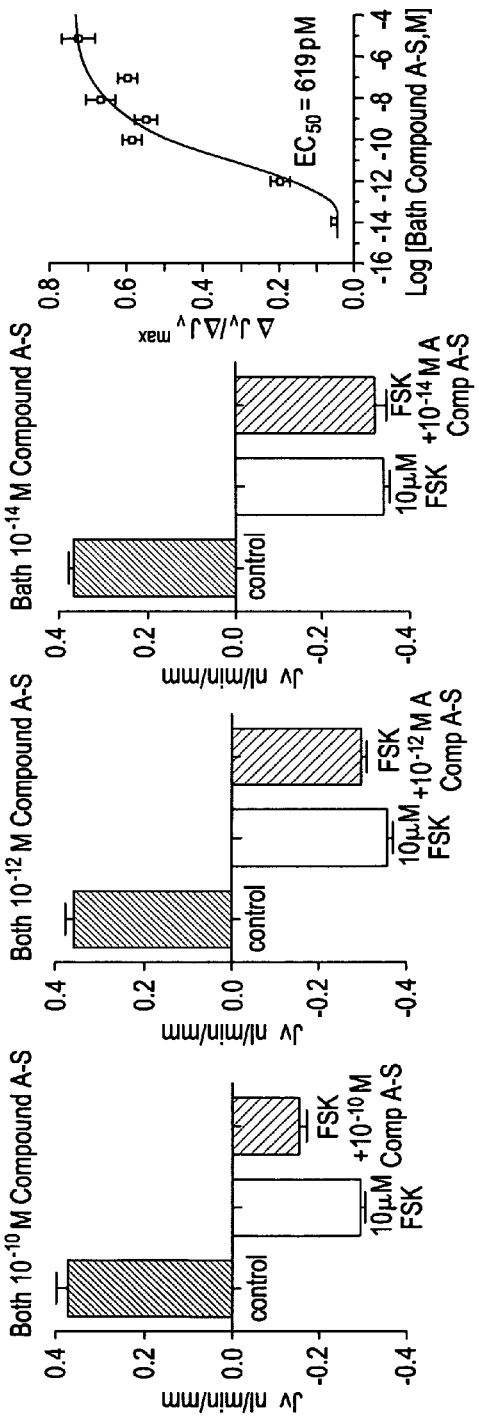

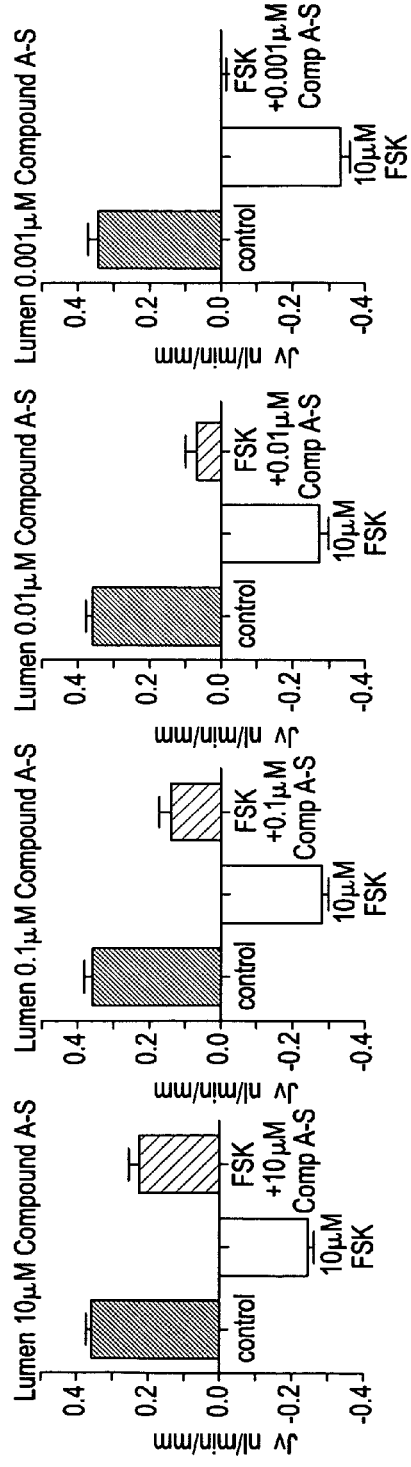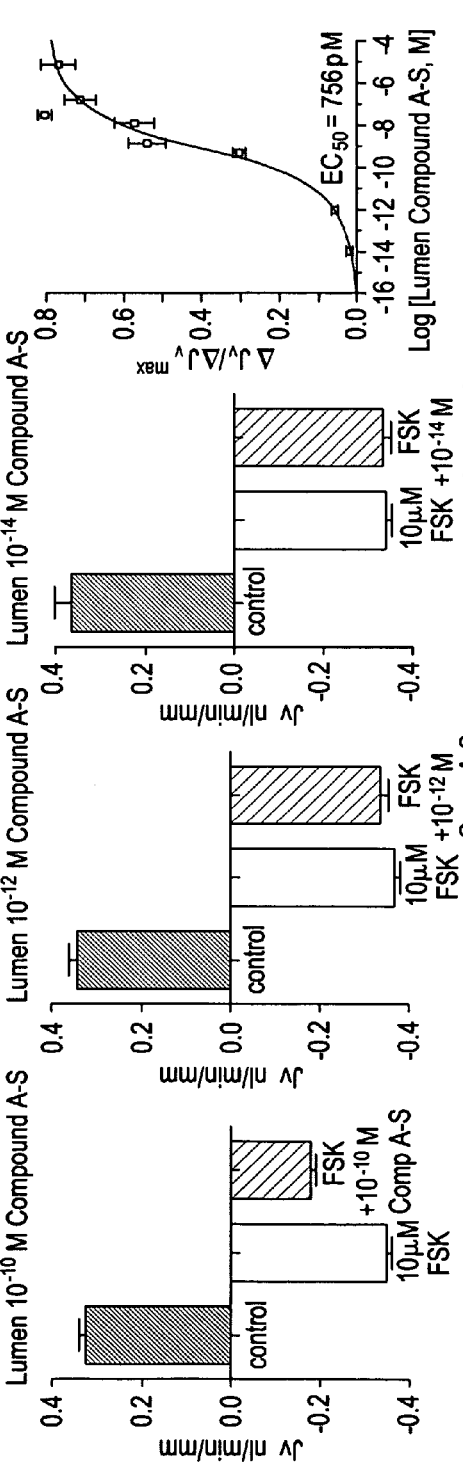

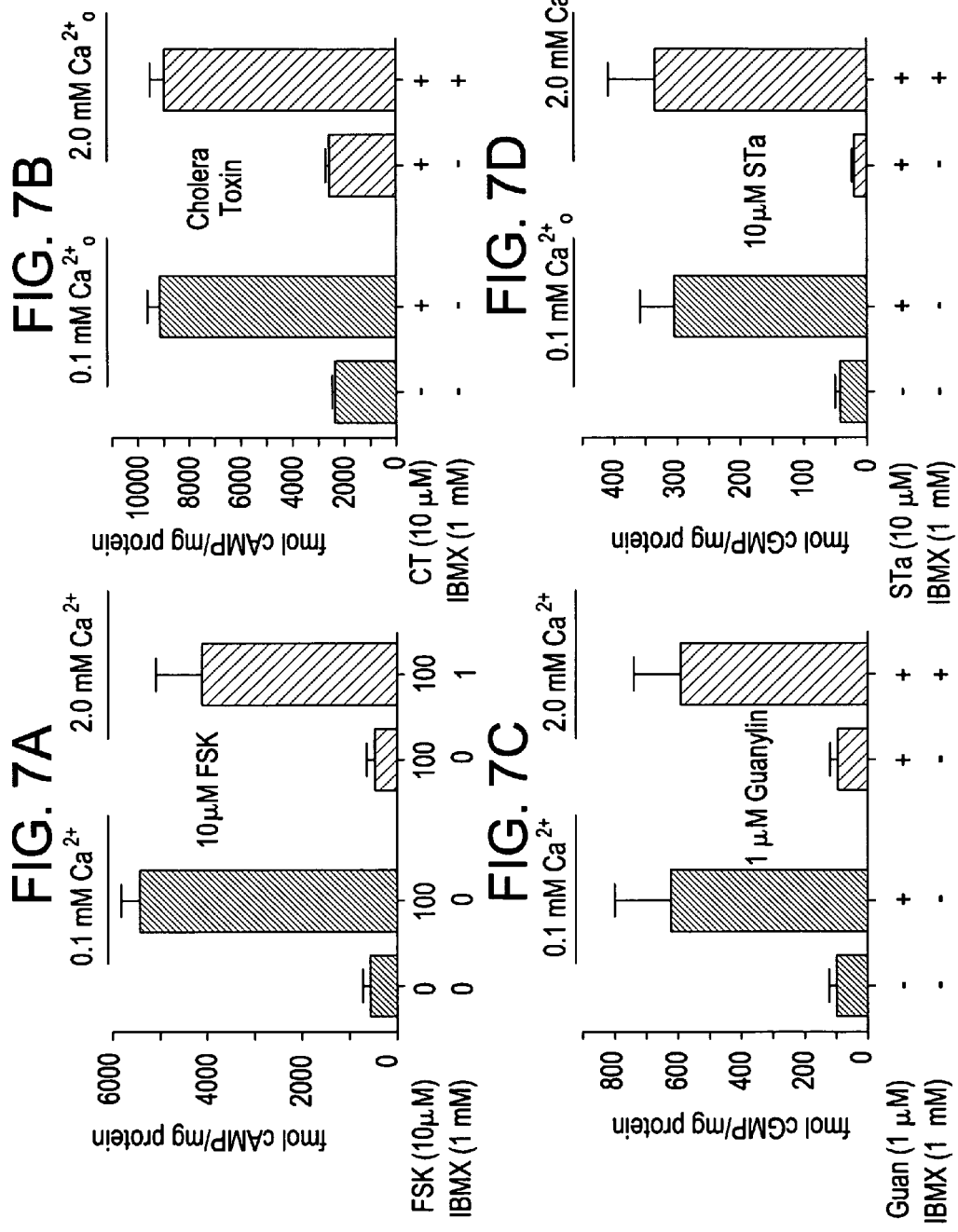

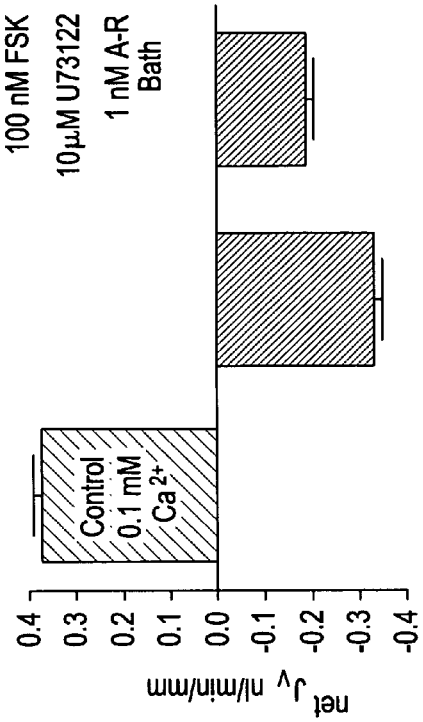
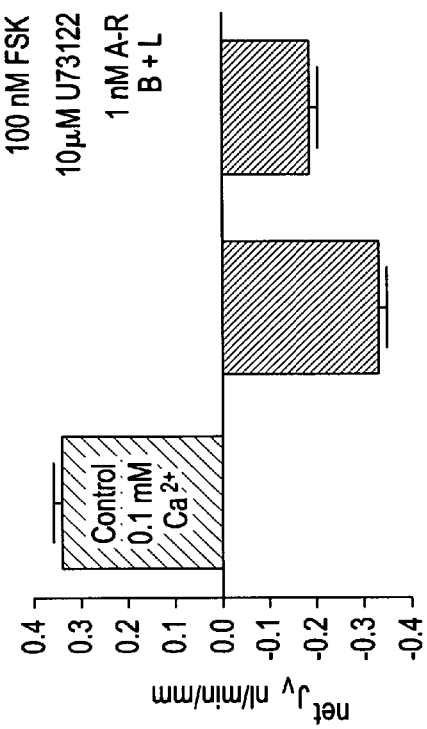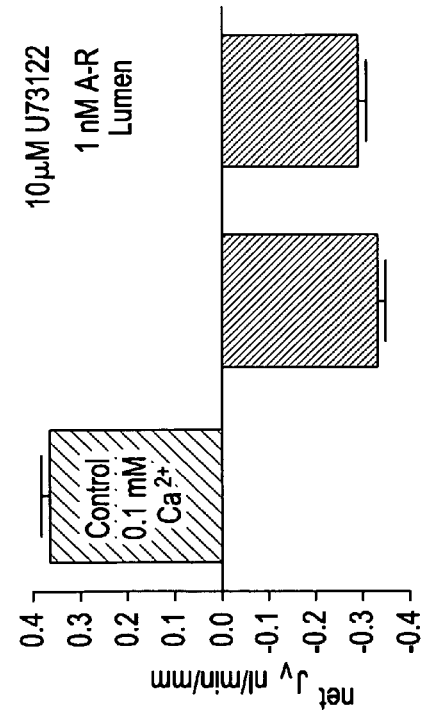
FIG. 9A
FIG. 9B
FIG. 9C

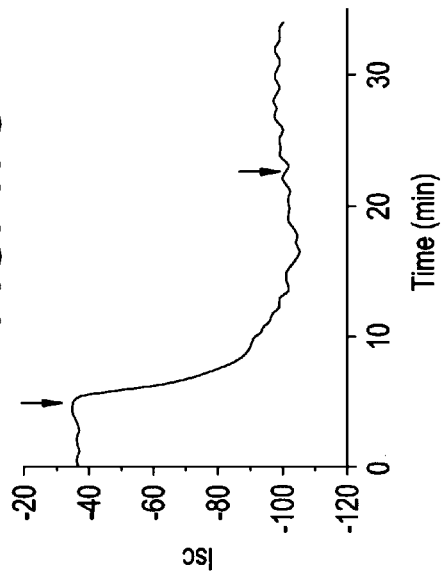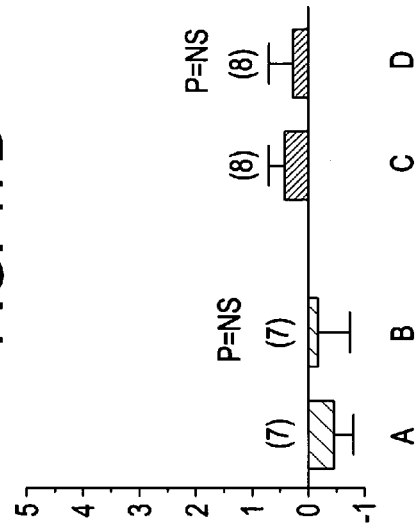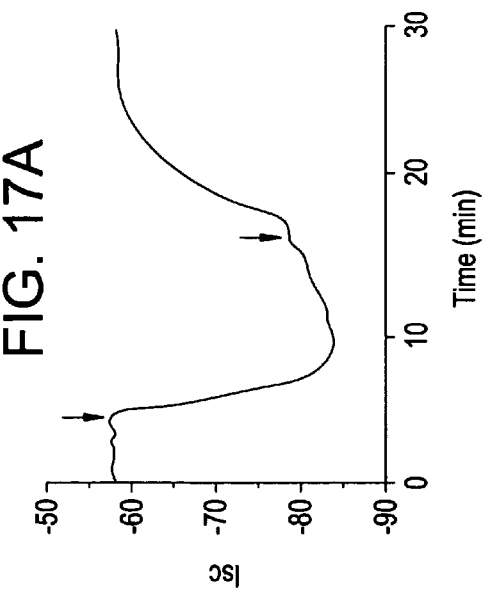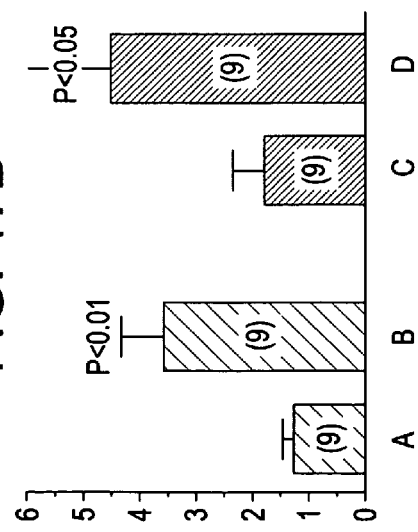

METHODS OF MODULATING INTESTINAL FLUID BALANCE

FIELD OF THE INVENTION

This invention relates generally to the field of medicine and, more specifically, to methods for treating or preventing intestinal fluid balance disorders and modulating intestinal fluid secretion and absorption.

BACKGROUND OF THE INVENTION

Many intestinal disorders result directly or indirectly from imbalances in finely tuned mechanisms of fluid balance in the intestinal tract, which is responsible for nutrient, electrolyte and fluid absorption, as well as the secretion of waste, excess electrolytes and fluid. The secretion and absorption run in parallel so that homeostasis is maintained. This balance is critical for preventing diarrhea and constipation, as well as malabsorption and malassimilation disorders.

Worldwide, diarrhea claims 3-5 million lives annually, mostly those of infants. Adequate fluid replacement could have prevented almost all of these deaths. Although its incidence is much lower in the more affluent nations, diarrhea remains one of the two most common reasons for visits to pediatric emergency departments and is also common among the elderly. Similar to diarrhea and enteric infections in patients with AIDS, diarrhea and enteric infections in children are associated with profound disruption of the intestinal absorptive surface, malnutrition and long term consequences, such as long-term impairments in growth and cognitive development in young children, and malabsorption of antiretroviral drugs in patients with AIDS. Diarrhea is among the most frequent health problems encountered by travelers. Up to 40% of short-term visitors to developing countries and up to 70% of long-term travelers will experience at least one bout of diarrhea.

While oral rehydration therapy can replace diarrheal losses, it does not facilitate reabsorption of secreted fluid and therefore does not lessen diarrhea. Antibiotics are of limited efficacy in many types of diarrhea and should not be used for treatment of diarrhea of less than five days' duration. Further, many antibiotics can worsen diarrhea. Finally, an effective oral vaccine is not available for epidemic infectious diarrheas.

Constipation is the most common gastrointestinal complaint in the United States and is of particular concern to the elderly. It often remains unrecognized until the patient develops anorectal disorders or diverticular disease. About 2% of the population describes constant or frequent intermittent episodes of constipation. Common treatments include bulk, stimulant, and osmotic laxatives, fecal softeners and lubricants. Chronic use of laxatives, however, is strongly discouraged, especially stimulant laxatives.

Many diseases directly or indirectly alter gastrointestinal physiology in such a manner that normal absorptive mechanisms are compromised, resulting in maldigestion or malabsorption of one or more dietary constituents. Typically, malabsorption can be the failure to absorb specific sugars, fats, proteins, or vitamins, or it can be a general malabsorption of food. Diarrhea, bloating or cramping, failure to thrive, frequent bulky stools, muscle wasting, and a distended abdomen may accompany malabsorption. Prolonged malabsorption can result in malnutrition and vitamin deficiencies. Two basic principles underlie the management of patients with malabsorption: (1) the correction of nutritional deficiencies and (2) when possible, the treatment of causative diseases (e.g., celiac disease, tropical sprue, Whipple's disease, pancreatic insufficiency and short bowel syndrome). However, if the treatment of the underlying disease of malabsorption were challenging due to, e.g., difficulties in diagnosing the disease, patients with malabsorption diseases would benefit from a treatment that addresses the correction of nutritional deficiencies.

SUMMARY OF THE INVENTION

The present invention provides methods for treating or preventing intestinal fluid balance disorders and modulating intestinal fluid secretion and absorption.

In one aspect, the invention provides methods of treating intestinal fluid balance disorders in a subject comprising administering an effective amount of a pharmaceutical composition comprising at least one calcimimetic or calcilytic compound together with a pharmaceutically acceptable carrier to the subject. In one aspect, the intestinal fluid balance disorder can be an abnormal intestinal motility. For example, the abnormal intestinal motility can be a diarrhea. In one aspect, the diarrhea can be an osmotic, secretory, exudative or a rapid transit diarrhea. In another aspect, the diarrhea can be an acute or chronic diarrhea. In a further aspect, the diarrhea can be a traveler's diarrhea. The diarrhea can be caused by exposure to one or more of a variety of infective agents, including *E. coli, Shigella, Salmonella, Campylobacter jejuni, Vibrio cholerae*, cholera toxin (CTX); *El Tor, Giardiasis, Entamoeba histolyca, cryptosporidium parvum*; Norwalk viruses, Rotaviruses, Adenoviruses, Caliciviruses, Astroviruses or Enteroviruses. In one aspect, the diarrhea can be cyclic AMP-mediated; or be associated with or resulting from a rise in cyclic GMP. In another aspect, the diarrhea can be caused by exposure to one or more non-infective agents that can affect the lower GI tract, such as antibiotics, anti-inflammatory medicine, caffeine, steroids, drugs or laxatives. In yet another aspect, the diarrhea can be caused by malabsorption or maldigestion. In a further aspect, the diarrhea can be caused by lactase deficiency or by short bowel syndrome. For example, the diarrhea can be associated with a gastrointestinal surgical procedure, such as an abdominal surgical procedure, or it can be associated with chemotherapy, radiation treatment, inflammation or toxic traumatic injury. In one aspect, the subject can be an infant or a child. In another aspect, the subject can be an adult or elderly.

In one aspect, the compound used to practice the methods of the invention can be a calcimimetic. In one aspect, the calcimimetic compound is a compound of the formula I

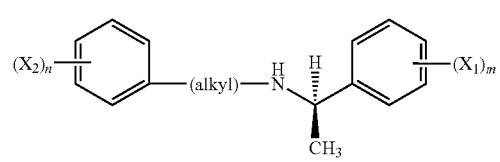

wherein $X_1$, $X_2$, n and m are as defined in Detailed Description, or a pharmaceutically acceptable salt thereof. In another aspect, the calcimimetic compound can be N-(3-[2-chlorophenyl]-propyl)-R-α-methyl-3-methoxybenzylamine or a pharmaceutically acceptable salt thereof. In a further aspect, the calcimimetic compound can be a compound of the formula II

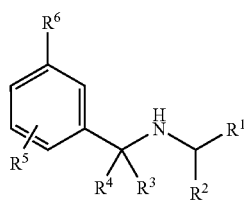

wherein $R^1$, $R^2$, $R^3$, $R^4$, $R^5$, and $R^6$ are as defined in Detailed Description, or a pharmaceutically acceptable salt thereof. In one aspect, the calcimimetic compound can be N-((6-(methyloxy)-4'-(trifluoromethyl)-1,1'-biphenyl-3-yl)methyl)-1-phenylethanamine, or a pharmaceutically acceptable salt thereof. In another aspect, the calcimimetic compound can be cinacalcet HCl. In one aspect, the compounds can be compounds disclosed in, for example, European Patent No. 637,237, 657,029, 724,561, 787,122, 907,631, 933,354, 1,203,761, 1,235 797, 1,258,471, 1,275,635, 1,281,702, 1,284,963, 1,296,142, 1,308,436, 1,509,497, 1,509,518, 1,553,078; International Publication Nos. WO 93/04373, WO 94/18959, WO 95/11221, WO 96/12697, WO 97/41090, WO 01/34562, WO 01/90069, WO 02/14259, WO 03/099776, WO 03/099814, WO 04/017908; WO 04/094362, WO 04/106280, U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,750,255, 6,908,935 and U.S. Patent Application Publication No. 2002/0107406, 2003/0008876, 2003/0144526, 2003/0176485, 2003/0199497, 2004/0006130, 2004/0077619, 2005/0032796, 2005/0107448, 2005/0143426, the disclosures of which are incorporated by reference herein.

Methods of the invention can be practiced, for example, wherein the abnormal intestinal motility is constipation. In one aspect, constipation can be associated with irritable bowel syndrome or intestinal motility disorders. In another aspect, constipation can be due to use of external agents such as opiates, antidepressants, calcium, or laxatives. In a further aspect, constipation can be due to a medical condition such as hypothyroidism, depression, hormone imbalance, diabetes mellitus, Hirschsprung's disease, pelvic floor dyssynergia, disruption of the blood supply, post-operative trauma, obstructing lesions, pseudo-obstruction or surgery. In another aspect, constipation can be due to a poor diet, overuse of coffee, tea, or alcohol, inactivity or lack of exercise.

In one aspect, the compound used to practice the methods of the invention can be a calcilytic. For example, calcilytic compounds useful for practicing methods of the present invention are those disclosed in European Patent and Publications Nos 637,237, 724,561, 901,459, 973,730, 1,258,471, 1,466,888, 1,509,518; International Publication Nos. WO 97/37967, WO 99/51569, WO 04/017908, WO 04/041755, WO 04/047751, WO 05/030746, WO 05/030749; U.S. Pat. Nos. 6,395,919, 6,432,656, 6,521,667, 6,750,255, 6,818,660, 6,864,267, 6,908,935, 6,916,956, and U.S. Patent Application Publication Nos. 2002/0099220, 2004/0009980, 2004/0014723, 2004/0192741, and 2005/0032850, 2005/0032850, the disclosures of which are incorporated by reference herein.

The invention further provides methods of modulating intestinal fluid secretion in a subject, comprising administering an effective amount of a pharmaceutical composition comprising at least one calcimimetic or calcilytic compound and a pharmaceutically acceptable carrier to the subject. In one aspect, fluid secretion can be increased and the administered compound can be a calcilytic. In another aspect, the fluid secretion is decreased and/or the fluid absorption is increased and the administered compound can be a calcimimetic. These methods can be used when, for example, the subject is prepared for a surgery.

The invention also provides methods of modulation of the absorption or secretion of a substance such as a drug, poison or nutrient in the intestinal tract of a subject, comprising administering an effective amount of a pharmaceutical composition comprising at least one calcimimetic or calcilytic compound together with a pharmaceutically acceptable carrier to the subject. In one aspect, the drug or nutrient absorption can be increased. In one aspect, the subject can be suffering from malnutrition or malassimilation. In one aspect, the compound is calcimimetic. In another aspect, the poison, drug or nutrient absorption can be decreased. For example, the compound used can be a calcilytic.

The invention further provides methods of treatment of a malassimilation or malnutrition of a subject, comprising administering an effective amount of a pharmaceutical composition comprising at least one calcimimetic or calcilytic compound together with a pharmaceutically acceptable carrier to the subject. In one aspect, the malassimilation can be due to mixing disorders, pancreatic insufficiency, reduced intestinal bile salt concentration, inadequate absorptive surface, mucosal absorptive defects, interrupted enterohepatic circulation of bile salts or lymphatic obstruction. In another aspect, the subject can be suffering from malnutrition.

In one aspect, the subject can be human, aquatic mammalian or non-aquatic animal.

BRIEF DESCRIPTION OF THE DRAWINGS

FIG. 3 schematically represents that the calcimimetic Compound A [N-(3-[2-chlorophenyl]-propyl)-α-methyl-3-methoxybenzylamine HCl] (R-stereoisomer) in bath abrogates toxin-induced fluid secretion in in vitro perfused rat colonic crypts.

FIG. 4 schematically represents that the calcimimetic Compound A (R-stereoisomer) in lumen abrogates toxin-induced fluid secretion in in vitro perfused rat colonic crypts.

FIG. 5 schematically represents that the calcimimetic Compound A (S-stereoisomer) in bath abrogates toxin-induced fluid secretion in in vitro perfused rat colonic crypts.

FIG. 6 schematically represents that the calcimimetic Compound A (S-stereoisomer) in lumen abrogates toxin-induced fluid secretion in in vitro perfused rat colonic crypts.

FIG. 7 demonstrates that activation of the CaSR by extracellular $Ca^{2+}$ reduces secretagogue-stimulated cyclic nucleotide accumulation.

FIG. 9 illustrates that PLC inhibitor blocks the effect of the calcimimetic on FSK-stimulated fluid secretion in rat colonic crypts.

FIG. 17 demonstrates that the ability of Compound A to reverse the forskolin-stimulated increase in the short-circuit current ($I_{sc}$) is abolished by TTX in 2-3 week old rats in the Ussing chamber model.

DETAILED DESCRIPTION OF THE INVENTION

I. Definitions

Figure 1:
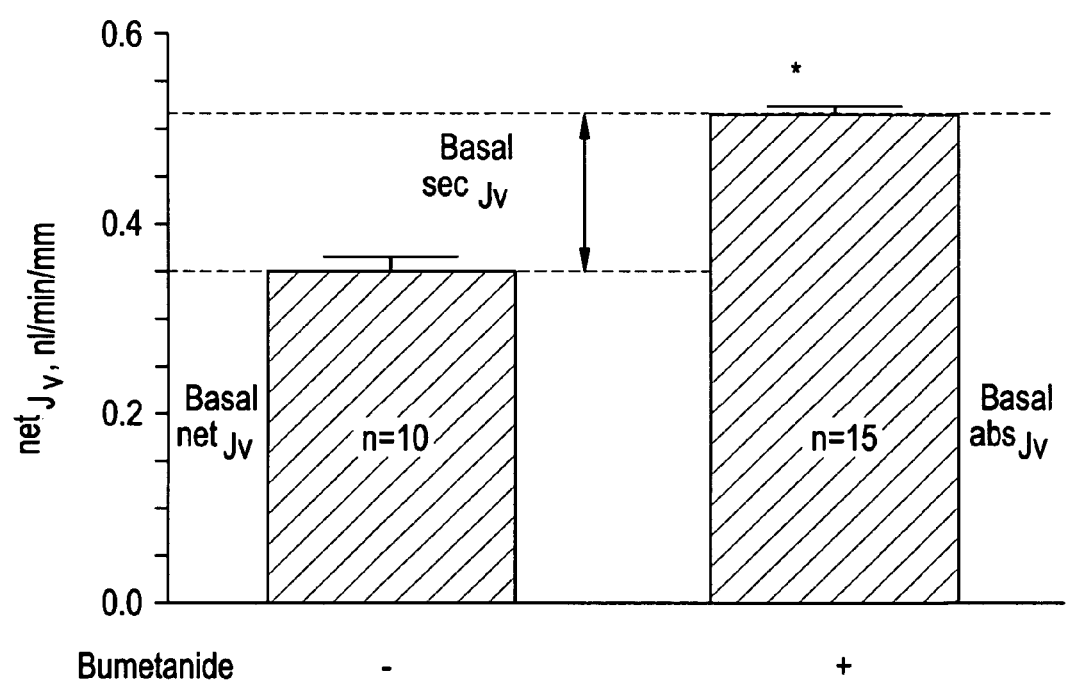
FIG. 1 illustrates measurements of net Jv, which is made up of two components, the absorptive basal $^{abs}$Jv and a secretory component $^{sec}$Jv.

As used herein, the term "subject" is intended to mean a human, an aquatic mammalian or a non-aquatic animal, in need of a treatment. This subject can have, or be at risk of developing, for example, intestinal fluid balance disorders.

"Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., Adv Pharmacol 47: 209-253, 2000).

The phrase "intestinal fluid balance disorders" refers to disorders that are characterized by abnormal fluid secretion or absorption in the intestinal tract and include, for example, diarrhea and constipation.

II. Calcimimetics and Calcilytic Compounds and Pharmaceutical Compositions Comprising them, Administration and Dosage A. Calcimimetic Compounds, Definitions As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less that 30 seconds (for example, by mobilizing internal calcium); it evokes a rapid increase in $[Ca^{2+}{}_i]$, occurring within thirty seconds; it evokes a sustained increase (greater than thirty seconds) in $[Ca^{2+}{}_i]$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}{}_i]$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V. In one aspect, a calcimimetic compound can be a small molecule. In another aspect, a calcimimetic can be an agonistic antibody to the CaSR.

Calcimimetic compounds useful in the present invention include those disclosed in, for example, European Patent No. 637,237, 657,029, 724,561, 787,122, 907,631, 933,354, 1,203,761, 1,235 797, 1,258,471, 1,275,635, 1,281,702, 1,284,963, 1,296,142, 1,308,436, 1,509,497, 1,509,518, 1,553,078; International Publication Nos. WO 93/04373, WO 94/18959, WO 95/11221, WO 96/12697, WO 97/41090, WO 01/34562, WO 01/90069, WO 02/14259, WO 02/059102, WO 03/099776, WO 03/099814, WO 04/017908; WO 04/094362, WO 04/106280, U.S. Pat. Nos. 5,688,938, 5,763, 569, 5,962,314, 5,981,599, 6,001,884, 6,011,068, 6,031,003, 6,172,091, 6,211,244, 6,313,146, 6,342,532, 6,362,231, 6,432,656, 6,710,088, 6,750,255, 6,908,935 and U.S. Patent Application Publication No. 2002/0107406, 2003/0008876, 2003/0144526, 2003/0176485, 2003/0199497, 2004/0006130, 2004/0077619, 2005/0032796, 2005/0107448, 2005/0143426, European patent application PCT/EP2006/004166, French patent application 0511940.

In certain embodiments, the calcimimetic compound is chosen from compounds of Formula I and pharmaceutically acceptable salts thereof:

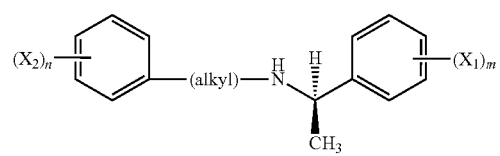

wherein:

$X_1$ and $X_2$, which may be identical or different, are each a radical chosen from $CH_3$, $CH_3O$, $CH_3CH_2O$, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, and acetyl radicals, or two of $X_1$ may together form an entity chosen from fused cycloaliphatic rings, fused aromatic rings, and a methylene dioxy radical, or two of $X_2$ may together form an entity chosen from fused cycloaliphatic rings, fused aromatic rings, and a methylene dioxy radical; provided that $X_2$ is not a 3-t-butyl radical;

n ranges from 0 to 5;

m ranges from 1 to 5; and the alkyl radical is chosen from C1-C3 alkyl radicals, which are optionally substituted with at least one group chosen from saturated and unsaturated, linear, branched, and cyclic C1-C9 alkyl groups, dihydroindolyl and thiodihydroindolyl groups, and 2-, 3-, and 4-piperid(in)yl groups.

The calcimimetic compound may also be chosen from compounds of Formula II:

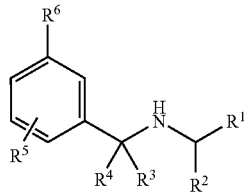

II and pharmaceutically acceptable salts thereof,
wherein:
$R^1$ is aryl, substituted aryl, heterocyclyl, substituted heterocyclyl, cycloalkyl, or substituted cycloalkyl;
$R^2$ is alkyl or haloalkyl;
$R^3$ is H, alkyl, or haloalkyl;
$R^4$ is H, alkyl, or haloalkyl;
each $R^5$ present is independently selected from the group consisting of alkyl, substituted alkyl, alkoxy, substituted alkoxy, halogen, —C(=O)OH, —CN, —NR$^d$S(=O)$_m$R$^d$, —NR$^d$C(=O)NR$^d$R$^d$, —NR$^d$S(=O)$_m$NR$^d$R$^d$, or —NR$^d$C(=O)R$^d$;
$R^6$ is aryl, substituted aryl, heterocyclyl, substituted heterocyclyl, cycloalkyl, or substituted cycloalkyl;
each $R^a$ is, independently, H, alkyl or haloalkyl;
each $R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;
each $R^c$ is, independently, alkyl, haloalkyl, phenyl or benzyl, each of which may be substituted or unsubstituted;
each $R^d$ is, independently, H, alkyl, aryl, aralkyl, heterocyclyl, or heterocyclylalkyl wherein the alkyl, aryl, aralkyl, heterocyclyl, and heterocyclylalkyl are substituted by 0, 1, 2, 3 or 4 substituents selected from alkyl, halogen, haloalkyl, alkoxy, cyano, nitro, $R^b$, —C(=O)R$^c$, —OR$^b$, —NR$^a$R$^a$, —NR$^a$R$^b$, —C(=O)OR$^c$, —C(=O)NR$^a$R$^a$, —OC(=O)R$^c$, —NR$^a$C(=O)R$^c$, —NR$^a$S(=O)$_n$R$^c$ and —S(=O)$_n$NR$^a$R$^a$;
m is 1 or 2;
n is 0, 1 or 2; and
p is 0, 1, 2, 3, or 4;
provided that if $R^2$ is methyl, p is 0, and $R^6$ is unsubstituted phenyl, then $R^1$ is not 2,4-dihalophenyl, 2,4-dimethylphenyl, 2,4-diethylphenyl, 2,4,6-trihalophenyl, or 2,3,4-trihalophenyl. These compounds are described in detail in published U.S. patent application No. 20040082625, which is incorporated herein by reference.

In one aspect of the invention the compound of Formula II can have the formula

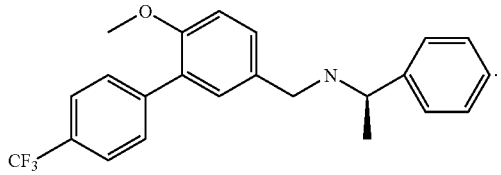 [SMILES: COc1ccc(CN[C@H](C)c2ccccc2)cc1-c1ccc(C(F)(F)F)cc1]

In certain embodiments of the invention the calcimimetic compound can be chosen from compounds of Formula III

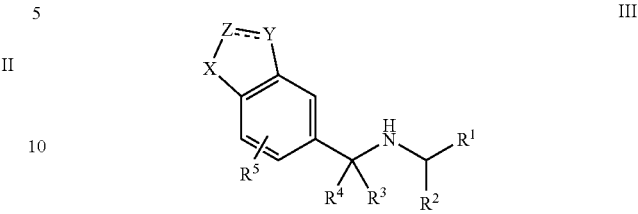

III and pharmaceutically acceptable salts thereof, wherein:
==== represents a double or single bond;
$R^1$ is $R^b$;
$R^2$ is C$_{1-8}$alkyl or C$_{1-4}$haloalkyl;
$R^3$ is H, C$_{1-4}$haloalkyl or C$_{1-8}$alkyl;
$R^4$ is H, C$_{1-4}$haloalkyl or C$_{1-4}$alkyl;
$R^5$ is, independently, in each instance, H, C$_{1-8}$alkyl, C$_{1-4}$haloalkyl, halogen, —OC$_{1-6}$alkyl, —NR$^a$R$^b$ or NR$^a$C(=O)R$^d$;
X is —CR$^d$=N—, —N=CR$^d$—, O, S or —NR$^d$—;
when ==== is a double bond then Y is =CR$^6$— or =N— and Z is —CR$^7$= or —N=; and when ==== is a single bond then Y is —CR$^a$R$^6$— or —NR$^d$— and Z is —CR$^a$R$^7$— or —NR$^d$—; and
$R^6$ is $R^d$, C$_{1-4}$haloalkyl, —C(=O)R$^c$, —OC$_{1-6}$alkyl, —OR$^b$, —NR$^a$R$^a$, —NR$^a$R$^b$, —C(=O)OR$^c$, —C(=O)NR$^a$R$^a$, —OC(=O)R$^c$, —NR$^a$C(=O)R$^c$, cyano, nitro, —NR$^a$S(=O)$_m$R$^c$ or —S(=O)$_m$NR$^a$R$^a$;
$R^7$ is $R^d$, C$_{1-4}$haloalkyl, —C(=O)R$^c$, —OC$_{1-6}$alkyl, —OR$^b$, —NR$^a$R$^a$, —NR$^a$R$^b$, —C(=O)OR$^c$, —C(=O)NR$^a$R$^a$, —OC(=O)R$^c$, —NR$^a$C(=O)R$^c$, cyano, nitro, —NR$^a$S(=O)$_m$R$^c$ or —S(=O)$_m$NR$^a$R$^a$; or
$R^6$ and $R^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from $R^5$; wherein when $R^6$ and $R^7$ form a benzo bridge, then the benzo bridge may be additionally substituted by a 3- or 4-atoms bridge containing 1 or 2 atoms selected from N and O, wherein the bridge is substituted by 0 or 1 substituents selected from C$_{1-4}$alkyl;
$R^a$ is, independently, at each instance, H, C$_{1-4}$haloalkyl or C$_{1-6}$alkyl;
$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from C$_{1-6}$alkyl, halogen, C$_{1-4}$haloalkyl, —OC$_{1-6}$alkyl, cyano and nitro;
$R^c$ is, independently, at each instance, C$_{1-6}$alkyl, C$_{1-4}$haloalkyl, phenyl or benzyl;
$R^d$ is, independently, at each instance, H, C$_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the C$_{1-6}$ alkyl, phenyl, benzyl, naphthyl and heterocycle are substituted by 0, 1, 2, 3 or 4 substituents selected from C$_{1-6}$alkyl, halogen, C$_{1-4}$haloalkyl, —OC$_{1-6}$alkyl, cyano and nitro, $R^b$, —C(=O)R$^c$, —OR$^b$, —NR$^a$R$^a$, —NR$^a$R$^b$, —C(=O)OR$^c$, —C(=O)NR$^a$R$^a$, —OC(=O)R$^c$, —NR$^a$C(=O)R$^c$, —NR$^a$S(=O)$_m$R$^c$ and —S(=O)$_m$NR$^a$R$^a$; and
m is 1 or 2.

Compounds of Formula III are described in detail in U.S. patent application 20040077619, which is incorporated herein by reference.

In one aspect, a calcimimetic compound is N-(3-[2-chlorophenyl]-propyl)-R-α-methyl-3-methoxybenzylamine HCl (Compound A). In another aspect, a calcimimetic compound is N-((6-(methyloxy)-4'-(trifluoromethyl)-1,1'-biphenyl-3-yl)methyl)-1-phenylethanamine (Compound B).

In one aspect, the calcimimetic compound of the invention can be chose from compounds of Formula IV

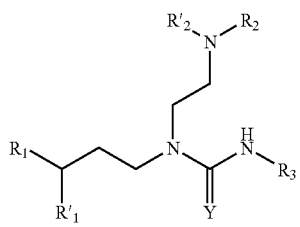

IV wherein:

Y is oxygen or sulphur;

$R_1$, and $R'_1$ are the same or different, and each represents an aryl group, a heteroaryl group, or $R_1$ and $R'_1$, together with the carbon atom to which they are linked, form a fused ring structure of formula:

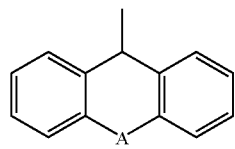

in which A represents a single bond, a methylene group, a dimethylene group, oxygen, nitrogen or sulphur, said sulphur optionally being in the sulphoxide or sulphone forms, wherein each of $R_1$ and $R'_1$, or said fused ring structure formed thereby, is optionally substituted by at least one substituent selected from the group c, wherein the group c consists of: halogen atoms, hydroxyl, carboxyl, linear and branched alkyl, hydroxyalkyl, haloalkyl, alkylthio, alkenyl, and alkynyl groups; linear and branched alkoxyl groups; linear and branched thioalkyl groups; hydroxycarbonylalkyl; alkylcarbonyl; alkoxycarbonylalkyl; alkoxycarbonyl; trifluoromethyl; trifluoromethoxy; —CN; —NO$_2$; alkylsulphonyl groups optionally in the sulphoxide or sulphone forms; wherein any alkyl component has from 1 to 6 carbon atoms, and any alkenyl or alkynyl components have from 2 to 6 carbon atoms, and wherein, when there is more than one substituent, then each said substituent is the same or different, $R_2$ and $R'_2$, which may be the same or different, each represents: a hydrogen atom; a linear or branched alkyl group containing from 1 to 6 carbon atoms and optionally substituted by at least one halogen atom, hydroxy or alkoxy group containing from 1 to 6 carbon atoms; an alkylaminoalkyl or dialkylaminoalkyl group wherein each alkyl group contains from 1 to 6 carbon atoms, or $R_2$ and $R'_2$, together with the nitrogen atom to which they are linked, form a saturated or unsaturated heterocycle containing 0, 1 or 2 additional heteroatoms and having 5, 6, or 7 ring atoms, said heterocycle being optionally substituted by at least one substituent selected from the group 'c' defined above, and wherein, when there is more than one substituent, said substituent is the same or different, $R_3$ represents a group of formula:

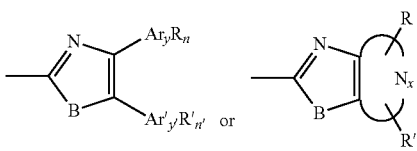

in which B represents an oxygen atom or a sulphur atom, x is 0, 1 or 2, y and y' are the same or different, and each is 0 or 1, Ar and Ar' are the same or different and each represents an aryl or heteroaryl group, n and n' are the same or different, and each is 1, when the y or y' with which it is associated is 0, or is equal to the number of positions that can be substituted on the associated Ar or Ar' when the said y or y' is 1, the fused ring containing $N_x$ is a five- or six-membered heteroaryl ring, and wherein R and R', which may be the same or different, each represent a hydrogen atom or a substituent selected from the group a, wherein the group a consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aralkoxy groups; aryloxy groups; alkoxycarbonyl; aralkoxycarbonyl; aryloxycarbonyl; hydroxycarbonylalkyl; alkoxycarbonylalkyl; aralkoxycarbonylalkyl; aryloxycarbonylalkyl; perfluoroalkyl; perfluoroalkoxy; —CN; acyl; amino, alkylamino, aralkylamino, arylamino, dialkylamino, diaralkylamino, diarylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aralkylamino, arylamino, dialkylamino, diaralkylamino, diarylamino, acylamino, trifluoromethylcarbonyl-amino, fluoroalkylcarbonylamino, or diacylamino group; CONH$_2$; alkyl-, aralkyl-, and aryl-amido groups; alkylthio, arylthio and aralkylthio and the oxidised sulphoxide and sulphone forms thereof; sulphonyl, alkylsulphonyl, haloalkylsulphonyl, arylsulphonyl and aralkylsulphonyl groups; sulphonamide, alkylsulphonamide, haloalkylsulphonamide, di(alkylsulphonyl)amino, aralkylsulphonamide, di(aralkylsulphonyl)amino, arylsulphonamide, and di(arylsulphonyl)amino; and saturated and unsaturated heterocyclyl groups, said heterocyclyl groups being mono- or bi-cyclic and being optionally substituted by one or more substituents, which may be the same or different, selected from the group b, wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group;

CONH$_2$; alkylamido groups; alkylthio and the oxidised sulphoxide and sulphone forms thereof; sulphonyl, alkylsulphonyl groups; and sulphonamide, alkylsulphonamide, and di(alkylsulphonyl)amino groups, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group.

Calcimimetic compounds useful in the methods of the invention include the calcimimetic compounds described above, as well as their stereoisomers, enantiomers, polymorphs, hydrates, and pharmaceutically acceptable salts of any of the foregoing.

B. Caclilytic Compounds, Definitions

As used herein, the term "calcilytic compounds" or "calcilytics" refers to compounds that inhibit, block, or decrease calcium sensing receptor (CaSR) activity, for examples, by causing a decrease in one or more calcium receptor activities evoked by extracellular Ca$^{2+}$. In one aspect, calcilytic may block, either partially or completely, the ability of increased concentrations of extracellular Ca$^{2+}$ to (a) increase [Ca$^{2+i}$]; (b) mobilize intracellular Ca$^{2+}$; (c) increase the formation of inositol-1,4,5-triphosphate; and (d) decrease dopamine or isoproterenol-stimulated cyclic AMP formation. In one aspect, a calcilytic compound can be a small molecule. In another aspect, a calcilytic can be an antagonistic antibody.

Calcilytic compounds useful in the present invention include those disclosed in, for example, European Patent and Publications Nos 637,237, 724,561, 901,459, 973,730, 1,258,471, 1,466,888, 1,509,518; International Publication Nos. WO 97/37967, WO 99/51569, WO 04/017908, WO 04/041755, WO 04/047751, WO 05/030746, WO 05/030749; U.S. Pat. Nos. 6,395,919, 6,432,656, 6,521,667, 6,750,255, 6,818,660, 6,864,267, 6,908,935, 6,916,956, and U.S. Patent Application Publication Nos. 2002/0099220, 2004/0009980, 2004/0014723, 2004/0192741, and 2005/0032850.

Calcilytic compounds useful in the methods of the invention include the calcilytic compounds described above, as well as their stereoisomers, enantiomers, polymorphs, hydrates, and pharmaceutically acceptable salts of any of the foregoing.

C. Methods of Assessing Calcimimetic and Calcilytic Activity

In one aspect, compounds binding at the CaSR-activity modulating site can be identified using, for example, a labeled compound binding to the site in a competition-binding assay format.

Calcimimetic or calcilytic activity of a compound can be determined using techniques such as those described in International Publications WO 93/04373, WO 94/18959 and WO 95/11211.

Other methods that can be used to assess compounds' calcimimetic or calcilytic activity are described below.

HEK 293 Cell Assay

HEK 293 cells engineered to express human parathyroid CaSR (HEK 293 4.0-7) have been described in detail previously (Nemeth E F et al. (1998) Proc. Natl. Acad. Sci. USA 95:4040-4045). This clonal cell line has been used extensively to screen for agonists, allosteric modulators, and antagonists of the CaSR (Nemeth E F et al. (2001) J. Pharmacol. Exp. Ther. 299:323-331).

For measurements of cytoplasmic calcium concentration, the cells are recovered from tissue culture flasks by brief treatment with 0.02% ethylenediaminetetraacetic acid (EDTA) in phosphate-buffered saline (PBS) and then washed and resuspended in Buffer A (126 mM NaCl, 4 mM KCl, 1 mM CaCl$_2$, 1 mM MgSO$_4$, 0.7 mM K$_2$HPO$_4$/KH$_2$PO$_4$, 20 mM Na-Hepes, pH 7.4) supplemented with 0.1% bovine serum albumin (BSA) and 1 mg/ml D-glucose. The cells are loaded with fura-2 by incubation for 30 minutes at 37° C. in Buffer A and 2 µM fura-2 acetoxymethylester. The cells are washed with Buffer B (Buffer B is Buffer A lacking sulfate and phosphate and containing 5 mM KCl, 1 mM MgCl$_2$, 0.5 mM CaCl$_2$ supplemented with 0.5% BSA and 1 mg/ml D-glucose) and resuspended to a density of 4 to 5×10$^6$ cells/ml at room temperature. For recording fluorescent signals, the cells are diluted five-fold into prewarmed (37° C.) Buffer B with constant stirring. Excitation and emission wavelengths are 340 and 510 nm, respectively. The fluorescent signal is recorded in real time using a strip-chart recorder.

For fluorometric imaging plate reader (FLIPR) analysis, HEK 293 cells are maintained in Dulbecco's modified Eagle's medium (DMEM) with 10% fetal bovine serum (FBS) and 200 µg/ml hygromycin. At 24 hrs prior to analysis, the cells are trypsinized and plated in the above medium at 1.2×10$^5$ cells/well in black sided, clear-bottom, collagen 1-coated, 96-well plates. The plates are centrifuged at 1,000 rpm for 2 minutes and incubated under 5% CO$_2$ at 37° C. overnight. Cells are then loaded with 6 µM fluo-3 acetoxymethylester for 60 minutes at room temperature. All assays are performed in a buffer containing 126 mM NaCl, 5 mM KCl, 1 mM MgCl$_2$, 20 mM Na-Hepes, supplemented with 1.0 mg/ml D-glucose and 1.0 mg/ml BSA fraction IV (pH 7.4).

In one aspect, the EC$_{50}$'s for the CaSR-active compounds can be determined in the presence of 1 mM Ca$^{2+}$. The EC$_{50}$ for cytoplasmic calcium concentration can be determined starting at an extracellular Ca$^{2+}$ level of 0.5 mM. FLIPR experiments are done using a laser setting of 0.8 W and a 0.4 second CCD camera shutter speed. Cells are challenged with calcium, CaSR-active compound or vehicle (20 µl) and fluorescence monitored at 1 second intervals for 50 seconds. Then a second challenge (50 µl) of calcium, CaSR-active compound, or vehicle can be made and the fluorescent signal monitored. Fluorescent signals are measured as the peak height of the response within the sample period. Each response is then normalized to the maximum peak observed in the plate to determine a percentage maximum fluorescence.

Bovine Parathyroid Cells

The effect of calcimimetic or calcilytic compounds on CaSR-dependent regulation of PTH secretion can be assessed using primary cultures of dissociated bovine parathyroid cells. Dissociated cells can be obtained by collagenase digestion, pooled, then resuspended in Percoll purification buffer and purified by centrifugation at 14,500×g for 20 minutes at 4° C. The dissociated parathyroid cells are removed and washed in a 1:1 mixture of Ham's F-12 and DMEM (F-12/DMEM) supplemented with 0.5% BSA, 100 U/ml penicillin, 100 µg/ml streptomycin, and 20 µg/ml gentamicin. The cells are finally resuspended in F-12/DMEM containing 10 U/ml penicillin, 10 µg/ml streptomycin, and 4 µg/ml gentamicin, and BSA was substituted with ITS+(insulin, transferrin, selenous acid, BSA, and linoleic acid; Collaborative Research, Bedford, Mass.). Cells are incubated in T-75 flasks at 37° C. in a humidified atmosphere of 5% CO$_2$ in air.

Following overnight culture, the cells are removed from flasks by decanting and washed with parathyroid cell buffer (126 mM NaCl, 4 mM KCl, 1 mM MgSO$_4$, 0.7 mM K$_2$HPO$_4$/KH$_2$PO$_4$, 20 mM Na-Hepes, 20; pH 7.45 and variable amounts of CaCl$_2$ as specified) containing 0.1% BSA and 0.5 mM CaCl$_2$. The cells are resuspended in this same buffer and portions (0.3 ml) are added to polystyrene tubes containing appropriate controls, CaSR-active compound, and/or varying concentrations of CaCl$_2$. Each experimental condition is performed in triplicate. Incubations at 37° C. are for 20 minutes and can be terminated by placing the tubes on ice. Cells are pelleted by centrifugation (1500×g for 5 minutes at 4° C.) and 0.1 ml of supernatant is assayed immediately. A portion of the cells is left on ice during the incubation period and then processed in parallel with other samples. The amount of PTH in the supernatant from tubes maintained on ice is defined as "basal release" and subtracted from other samples. PTH is measured according to the vendor's instructions using rat PTH-(1-34) immunoradiometric assay kit (Immunotopics, San Clemente, Calif.).

MTC 6-23 Cell Calcitonin Release

Rat MTC 6-23 cells (clone 6), purchased from ATCC (Manassas, Va.) are maintained in growth media (DMEM high glucose with calcium/15% HIHS) that is replaced every 3 to 4 days. The cultures are passaged weekly at a 1:4 split ratio. Calcium concentration in the formulated growth media is calculated to be 3.2 mM. Cells are incubated in an atmosphere of 90% O$_2$/10% CO$_2$, at 37° C. Prior to the experiment, cells from sub-confluent cultures are aspirated and rinsed once with trypsin solution. The flasks are aspirated again and incubated at room temperature with fresh trypsin solution for 5-10 minutes to detach the cells. The detached cells are suspended at a density of 3.0×10$^5$ cells/mL in growth media and seeded at a density of 1.5×10$^5$ cells/well (0.5 mL cell suspension) in collagen-coated 48 well plates (Becton Dickinson Labware, Bedford, Mass.). The cells are allowed to adhere for 56 hours post-seeding, after which the growth media was aspirated and replaced with 0.5 mL of assay media (DMEM high glucose without/2% FBS). The cells are then incubated for 16 hours prior to determination of calcium-stimulated calcitonin release. The actual calcium concentration in this media is calculated to be less than 0.07 mM. To measure calcitonin release, 0.35 mL of test agent in assay media is added to each well and incubated for 4 hours prior to determination of calcitonin content in the media. Calcitonin levels are quantified according to the vendor's instructions using a rat calcitonin immunoradiometric assay kit (Immutopics, San Clemente, Calif.).

Inositol Phosphate Assay

The calcimimetic or calcilytic properties of compounds could also be evaluated in a biochemical assay performed on Chinese hamster ovarian (CHO) cells transfected with an expression vector containing cloned CaSR from rat brain [CHO(CaSR)] or not [CHO(WT)] (Ruat M., Snowman A M., J. Biol. Chem 271, 1996, p 5972). CHO(CaSR) has been shown to stimulate tritiated inositol phosphate ([$^3$H]IP) accumulation upon activation of the CaSR by Ca$^{2+}$ and other divalent cations and by NPS 568 (Ruat et al., J. Biol. Chem 271, 1996). Thus, [$^{3H}$]IP accumulation produced by 10 µM of each CaSR-active compound in the presence of 2 mM extracellular calcium can be measured and compared to the effect produced by 10 mM extracellular calcium, a concentration eliciting maximal CaSR activation (Dauban P. et al., Bioorganic & Medicinal Chemistry Letters, 10, 2000, p 2001).

D. Pharmaceutical Compositions and Administration

Calcimimetic and calcilytic compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methanesulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J Pharm. Sci.* 66: 1, 1977. In certain embodiments of the invention salts of hydrochloride and salts of methanesulfonic acid can be used.

In some aspects of the present invention, the calcium-receptor active compound can be chosen from cinacalcet, i.e., N-(1-(R)-(1-naphthyl)ethyl]-3-[3-(trifluoromethyl)phenyl]-1-aminopropane, cinacalcet HCl, and cinacalcet methanesulfonate. The calcimimetic compound, such as cinacalcet HCl and cinacalcet methanesulfonate, can be in various forms such as amorphous powders, crystalline powders, and mixtures thereof. The crystalline powders can be in forms including polymorphs, psuedopolymorphs, crystal habits, micromeretics, and particle morphology.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

In some aspects of the present invention, the compositions disclosed herein comprise a therapeutically effective amount of a calcium receptor-active compound for the treatment or prevention of diarrhea. For example, in certain embodiments, the calcimimetic compound such as cinacalcet HCl can be present in an amount ranging from about 1% to about 70%, such as from about 5% to about 40%, from about 10% to about 30%, or from about 15% to about 20%, by weight relative to the total weight of the composition.

The compositions useful in the invention may contain one or more active ingredients in addition to the calcium sensing receptor-active compound. The additional active ingredient may be another calcimimetic or calcilytic compound, or it may be an active ingredient having a different therapeutic activity. Examples of such additional active ingredients include vitamins and their analogs, such as antibiotics, lanthanum carbonate, anti-inflammatory agents (steroidal and non-steroidal) and inhibitors of pro-inflammatory cytokine (ENBREL®, KINERET®). When administered as a combination, the therapeutic agents can be formulated as separate compositions that are given at the same time or different times, or the therapeutic agents can be given as a single composition.

In one aspect, the pharmaceutical compositions useful for methods of the invention may include additional compounds for slowing the transit time through the gastrointestinal tract, thereby prolonging residence time and promoting contact of the compositions of the invention. Examples of such compounds are described, e.g., in the U.S. Patent Application publication No. 20030013676. In one aspect, the compositions may include cGMP (i.e., cyclic guanosine 3',5'-cyclic monophosphate; guanosine 3',5'-monophosphate; 3',5'-GMP; cGMP; guanosine 3',5'-(hydrogen phosphate); guanosine 3',5'-cyclic monophosphate; and guanosine 3',5'-cyclic phosphate).

In another aspect, the compounds used to practice the methods of the instant invention can be formulated for oral administration that release biologically active ingredients in the colon without substantial release into the upper gastrointestinal tract, e.g. stomach and intestine. For example, the pharmaceutical compositions of the invention can be used with the drug carrier including pectin and galactomannan, polysaccharides that are both degradable by colonic bacterial enzymes (U.S. Pat. No. 6,413,494). While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, polygalacturonic acid, tragacanth gum, arabic gum, and a mixture thereof), which is degradable by colonic enzymes (U.S. Pat. No. 6,319,518).

III. Methods of Treatment

In one aspect, the invention provides methods for treatment of intestinal fluid balance disorders in a subject. Under normal physiological conditions, approximately 1.5 L of fluid enters the colon each day, but only about 100-200 mL is excreted in the stool. The regulation of water and electrolyte transport in the colon involves the complex interplay between humoral, paracrine and neural regulatory pathways. Intestinal fluid balance disorders are characterized by abnormal fluid secretion or absorption in the intestinal tract and include, for examples, diarrhea and constipation.

A. Diarrhea

In one aspect, the invention provides methods for treating abnormal intestinal motilities disorders such as diarrhea. The methods of the invention comprise administering to the individual a therapeutically effective amount of a calcimimetic compound.

As used herein, the term "diarrhea" refers to a condition of three or more unformed stools in a 24-hour period of volume more than 200 g per day. In one aspect, diarrhea can be osmotic, i.e., resulting if the osmotic pressure of intestinal contents is higher than that of the serum. This condition may result from malabsorption of fat (e.g., in celiac disease) or of lactose (e.g., in intestinal lactase deficiency), or it can happen due to the use of certain laxatives (e.g., lactulose, magnesium hydroxide) or artificial sweeteners (e.g., sorbitol, mannitol). In another aspect, diarrhea can be secretory, i.e., occurring when there is a net secretion of water into the lumen. This may occur with bacterial toxins (such as those produced, e.g., by *E. coli* and *Vibrio cholerae*), or with hormones, such as vasoactive intestinal polypeptide, which is produced by rare islet cell tumors (pancreatic cholera). Both osmotic and secretory diarrheas result from abnormalities in the small intestine such that the flow of water through the ileocecal area overcomes the absorptive capacity of the colon.

In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with chemotherapy, radiation treatment, inflammation or toxic traumatic injury. In another aspect, exudative diarrhea can be associated with a gastrointestinal or abdominal surgery.

In another aspect, diarrhea can be due to acceleration of intestinal transit (rapid transit diarrhea). Such condition may occur because the rapid flow-through impairs the ability of the gut to absorb water.

As used herein, the term "acute diarrhea" refers to a condition characterized by stool weight more than 200 g/day for less than 14 days duration, usually associated with an increased frequency of bowel movements. Exemplary causes of acute diarrhea are summarized in Table 1 below.

TABLE 1

Common causes of acute diarrhea

| | |
|---|---|
| Drugs | Laxatives, Antacids, Antibiotics, Cholinergic drugs, Lactose, uanethidine, Quinidine, Digitalis, Colchicine, otassium supplements, Lactulose |
| Bacteria (toxin-mediated, cytotonic) | Enterotoxigenic *Escherichia coli* (both heat-labile and heat-stable toxins), *Vibrio cholerae*, *Vibrio parahaemolyticus*, *Clostridium perfringens*, *Bacillus cereus* |
| Bacteria (toxin-mediated, cytotoxic) | *Clostridium difficile*, *Staphylococcus aureus*, *Shigella dysenteriae*, *Campylobacter jejuni*, *Yersinia enterocolitica* |
| Bacteria (invasive) | *Salmonella*, enteroinvasive *Escherichia coli* |
| Bacteria (unknown mechanism) | Enteropathogenic *Escherichia coli*, Enteroadherent *Escherichia coli* |
| Viruses | Parvovirus (Norwalk agent), Reovirus (rotavirus), Adenovirus, Calicivirus, Astrovirus, Enterovirus |
| Protozoa | *Cryptosporidia*, *Giardia lamblia*, *Entamoeba histolytica*, El Tor |
| Parasites | *Strongyloides*, *Trichuris* |

As used herein, the term "traveler's diarrhea" refers to a syndrome characterized by an increase in frequency of unformed bowel movements, typically, four to five loose stools per day, with associated symptoms including abdominal cramps, nausea, bloating, urgency, fever and malaise. Traveler's diarrhea can be characterized by an abrupt beginning, during travel or soon after returning home. In one aspect, it can be caused by enterotoxigenic *E. coli*. In another aspect, it can be caused by *Salmonella gastroenteritis*, *Shigella dysentery*, or viral enteric pathogens.

As used herein, the term "chronic diarrhea" refers to a condition characterized by stool weight more than 200 g/day for more than 14 days duration, usually associated with an increased frequency of bowel movements. Pathophysiological mechanisms of chronic diarrhea are summarized in Table 2 below.

TABLE 2

Pathophysiological mechanisms of chronic diarrhea

| Major Disturbance | Probable Causes/Mechanisms | Examples/Associated Conditions |
|---|---|---|
| Osmotic | Ingestion | Antacids, laxatives |
| | Maldigestion | Pancreatic insufficiency, disaccharidase deficiency |
| | Malabsorption | Carbohydrate malabsorption, congenital chloridorrhea |
| Disorders of intestinal transit | Slow transit ("blind loop syndrome") - excessive contact time | Fistulas, strictures (such as in the patient with Crohn's disease), diabetic neuropathy |
| | Rapid transit - insufficient contact time | Intestinal resection, hyperthyroidism, irritable bowel |
| Secretory | Bacterial enterotoxins | *Vibrio cholerae*, enterotoxigenic *E. coli* |
| | Secretagogues | Bile acids, fatty acids, ethanol, prostaglandins, phenolphthalein, dioctyl sodium sulfosuccinate, VIP, gastrin, calcitonin |
| Exudative | Increased passage of body fluids into lumen | Ulcerative colitis, Crohn's disease |

In one aspect, diarrhea can be cyclic AMP-mediated. In another aspect, diarrhea can be associated with or resulting from a rise in cyclic GMP. In a further aspect, diarrhea can be caused by anti-inflammatory medicine, caffeine, steroids, drugs or laxatives. In another aspect, diarrhea can be caused by short bowel syndrome.

In one aspect, the invention provides methods of treating abnormal gastric fluid secretion/absorption disorders in conjunction with treating underlying causes of, for example, diarrhea or with other treatment methods. In one aspect, calcimimetics can be administered to a subject before, after or concurrently with oral rehydration therapy. For example, oral rehydration therapy may contain the following ingredients: sodium, potassium, chloride, bicarbonate, citrate and glucose. In another aspect, calcimimetics can be administered to a subject before, after or concurrently with an antimotility agent, such as loperamide (Imodium), diphenoxylate, or bismuth subsalicylate (Pepto-Bismol). In another aspect, calcimimetics can be administered with antibiotics (e.g., trimethoprim-sulfamethoxazole (Bactrim DS), ciprofloxacin (Cipro), norfloxacin (Noroxin), ofloxacin (Floxin), doxycycline (Vibramycin), erythromycin). In one aspect, a calcimimetic compound can be administered together with calcium or polyamines such as spermine, spermidine, putrescine, and ornithine metabolites or amino acids such of L-tryptophan, L-phenylalanine. In another aspect, a calcimimetic compound can be administered together with sodium and glucose.

In addition, calcimimetics may be administered in conjunction with surgical and non-surgical treatments.

B. Constipation

The invention also provides methods for treating abnormal intestinal motilities disorders such as constipation. The methods of the invention comprise administering to a subject a therapeutically effective amount of a calcilytic compound.

As used herein, the term "constipation" refers to persistent symptoms of difficult, infrequent (fewer than 3 times per week) or seemingly incomplete stool evacuation. In one aspect, the stool can be hard, difficult to pass, scybalous, and can be accompanied by abdominal pain. Some common causes of chronic constipation are summarized in Table 3.

TABLE 3

| | Causes of chronic constipation |
|---|---|
| Functional Motility disorders of unknown mechanism | Irritable bowel syndrome<br>Atonic colon<br>Failure of defecation (obstruction by hyperactive anal sphincter; impaired rectoanal reflex) |
| Pharmaco-logic | Opiates, antidepressants, narcotics, calcium, laxative abuse, poor dietary habits, inadequate water intake, inadequate fiber intake, overuse of coffee, tea, or alcohol, iron supplements, nonmagnesium antacids, calcium channel blockers, inadequate thyroid hormone supplementation, anticholinergic drugs |
| Organic | Endocrine dysfunction (hypothyroidism), neurologic dysfunction (diabetic autonomic neuropathy, spinal cord injury, head injury, cerebrovascular accident, multiple sclerosis, Parkinson disease), depression, Hirschsprung's disease, Chagas disease, pseudo-obstruction (hollow viscera myopathy, hollow viscera neuropathy), obstructing lesions (e.g . . . , carcinoma, diverticulitis) |

In one aspect, the invention provides methods for treating constipation in combinations with methods for treatment of underlying diseases. For example, the invention provides methods comprising administering calcilytic to a subject in conjunction with changes in the subject's diet, such as the addition of sufficient bulk (i.e., insoluble fiber). In one aspect, a calcilytic can be used together with a laxative.

C. Methods of Modulating Intestinal fluid Secretion and Absorption

The invention further provides methods for modulating intestinal fluid secretion and absorption. In one aspect, the purpose can be to increase fluid absorption and/or decrease fluid secretion in a subject and thus the methods of the invention can comprise administering an effective amount of a pharmaceutical composition comprising a calcimimetic compound.

In another aspect, the purpose can be to increase intestinal fluid secretion or reduce intestinal fluid absorption, and therefore the method of the invention can comprise administering an effective amount of a pharmaceutical composition comprising a calcilytic compound. In one aspect, the method can be used in conjunction with the preparation of an individual for a surgery, for example, for an abdominal surgery or a colonoscopy. In addition, the method can be used to prepare the bowel for radiographic examination.

D. Malabsorption and Malassimilation

The invention provides methods of modulation the absorption or secretion of a drug, poison or nutrient in the intestinal tract of a subject, comprising administering an effective amount of a pharmaceutical composition comprising at least one calcimimetic or calcilytic compound together with a pharmaceutically acceptable carrier to the subject.

In one aspect, the drug or nutrient absorption is increased and the compound administered is a calcimimetic. In one aspect, the invention provides methods of treatment of a malassimilation or a malabsorption of a subject, comprising administering an effective amount of a pharmaceutical composition comprising at least one calcimimetic together with a pharmaceutically acceptable carrier to the subject.

As used herein, the term "malassimilation" encompasses impaired processes of food digestions and absorption occurring in one of two ways (1) through intraluminal disorders (maldigestion of food) and (2) through intramural disorders (malabsorption of food). Clinical manifestations of malassimilation are summarized in Table 4.

TABLE 4

| Classification of malassimilation syndromes | |
|---|---|
| Defective intraluminal digestion | Defective intramural absorption |
| Mixing disorders | Inadequate absorptive surface |
| Postgastrectomy | Intestinal resection or bypass |
| Pancreatic insufficiency | Mesenteric vascular disease with |
| Primary (Cystic fibrosis) | massive intestinal resection |
| Secondary (Chronic pancreatitis | Regional enteritis with multiple bowel resections |
| Pancreatic carcinoma | |
| Pancreatic resection) | Jejunoileal bypass |
| Reduced intestinal bile salt | Mucosal absorptive defects |
| concentration | Biochemical or genetic abnormalities |
| Liver disease | Celiac disease |
| Hepatocellular disease | Disaccharidase deficiency |
| Cholestasis (intrahepatic or | Hypogammaglobulinemia |
| extrahepatic) | Abetalipoproteinemia |
| Abnormal bacterial proliferation in the | Hartnup disease |
| small bowel | Cystinuria |
| Afferent loop stasis | Monosaccharide malabsorption |
| Strictures | Inflammatory or infiltrative disorders |
| Fistulas | Regional enteritis |
| Blind loops | Amyloidosis |
| Multiple diverticula of the small bowel | Scleroderma |
| Hypomotility states (diabetes, | Lymphoma |
| scleroderma, intestinal pseudo- | Radiation enteritis |
| obstruction) | Eosinophilic enteritis |
| Interrupted enterohepatic circulation of | Tropical sprue |
| bile salts | Infectious enteritis (e.g., |
| Ileal resection | *salmonellosis*) |
| Ileal inflammatory disease (regional | Collagenous sprue |
| ileitis) | Nonspecific ulcerative jejunitis |
| Drugs (by sequestration or precipitation | Mastocytosis |
| of bile salts) | Dermatologic disorders (e.g., |
| Neomycin | dermatitis herpetiformis) |
| Calcium carbonate | Lymphatic obstruction |
| Cholestyramine | Intestinal lymphangiectasia Whipple's disease Lymphoma |

In one aspect, the invention provides methods of treating malassimilation of a subject, comprising administering an effective amount of a pharmaceutical composition comprising a calcimimetic compound together with a pharmaceutically acceptable carrier to the subject. In one aspect, methods of the invention can be practiced in combination with the methods of treatment of underlying causes of malassimilation. For example, methods of the invention can be practiced in conjunction with dietary restrictions (e.g., in cases of carbohydrate or fat intolerance). In another aspect, a calcimimetic can be administered in combination with antibiotics (e.g., gentamicin), bile acid-binding agents (e.g., cholestyramine), or digestive enzymes (e.g., pancrelipase).

Methods of the invention comprising administering a pharmaceutical composition comprising a calcimimetic can also be practiced to treat malnutrition in a subject. For example, a subject can be malnourished if the subject is grossly underweight (weight for height is below 80% of the standard), grossly overweight (weight for height above 120% of the standard), if the subject unintentionally lost 10% or more of body weight, has a gastrointestinal tract surgery, experienced nutrient losses (e.g., from diarrhea, dialysis, vomiting), has increased metabolic needs (e.g., due to pregnancy, lactation, increased physical activity, fever, injury), is an alcoholic or chronic drug user (antibiotics, antidepressants, diuretics), has medical conditions which interfere with nutrient intake, absorption, metabolism, or utilization, has poor dentition (particularly in the elderly subjects), or has mouth sores due to herpes, HIV or chemotherapy. In another aspect, the subject can be malnourished due to dietary risk factors (e.g., loss of appetite, inadequate food or nutrient intake, lack of variety of foods, fad, weight-loss diets, inadequate fiber, excessive fat, sodium, sugar, excess alcohol, eats too few fruits, vegetables) or due to social risk factors (e.g., chronic ill health, poverty, inadequate money to buy food, low socioeconomic status, immobility or inability to purchase, store, or cook food, social isolation, eats alone most of the time, substance abuser, conditions which limit subject's ability to eat). Further, the methods of the invention can be practiced when a subject has limited access to nutrients such as during survival following environmental disasters, survival at sea, marooning and deep-sea living or space travel.

The methods of the invention comprising administering pharmaceutical composition comprising a calcilytic compound can be practiced, for example, to reduce intestinal absorption of a drug, chemical or nutrient in a subject. In one aspect, the subject can be overweight. In another aspect, the subject can be at risk because of ingestion of a poison or drug.

The following examples are offered to more fully illustrate the invention, but are not to be construed as limiting the scope thereof.

EXAMPLE 1

This example outlines methods for crypt isolation and perfusions, methods for assessing fluid secretion and absorption in a variety of species and methods for assessing calcimimetic and calcilytic properties of compounds. The effect of calcimimetic or calcilytic compounds on CaSR-dependent regulation of net fluid movement ($J_v$), changes in intracellular calcium and IP3 accumulation can be assessed using freshly isolated colonic crypts or dispersed colonocytes.

Methods for Crypt Isolation and Perfusion in Vitro

Non-fasting male Sprague-Dawley rats weighing between 150-200 g or mice weighing 20-30 g were used in all experiments. The same protocol can be followed for either rats or mice. Following sacrifice, individual crypts are obtained from the distal colon by hand dissection. Net fluid movement (Jv) is determined using the microperfusion methods previously described in detail for colonic crypts, renal tubules and gastric glands (Geibel, J. et al. 1989 Am. J. Physiol 257:F790-F797; Boron, W. F. et al., 1994. J. Exp. Biol. 196:347-360). Briefly, single, hand-dissected crypts are placed in a temperature-controlled chamber on the stage of an inverted microscope. An assembly of concentric glass micropipettes is used to hold the blind end of the crypt. The perfusion pipette is used to puncture this blind end and introduce the perfusate containing methoxy-$^3$H-inulin into the crypt lumen in an anterograde direction. A second set of micropipettes is used to cannulate the open end of the crypt and collect the effluent. Following cannulation lumen and bath solutions flows continuously at 4-10 nl/min and 5 ml/min, respectively. The effluent is sampled with a volume-calibrated pipette. Jv is determined from the length and diameter of the crypt, the rate at which the effluent accumulated in the collection pipette and from the concentration of methoxy-$^3$H-inulin in the perfusate and effluent. [Methoxy-$^3$H-inulin] was determined in a scintillation counter. The bath (fluid on the blood side of the colonic crypt, i.e., not lumen) is also collected to control for leakage from either the perfusion pipette or from the crypt. Experiments are discarded whenever bath [methoxy-$^3$H-inulin] exceeded background. Jv is expressed as nl/mm·min. Each data point represents the average of three five-minute collections of effluent. Positive values represent net absorption, while negative values represent net secretion.

At least five crypts are studied in each experimental protocol. At the end of each experiment the viability of the crypt is assessed with trypan blue and experiments in which cells failed to exclude dye were discarded; fewer than 15% of crypts are discarded.

Freshly Isolated Colonic Crypts or Colonocytes from Rat, Mouse or Human

Colons are removed from rats or mice or surgical specimens obtained from human, cut open longitudinally, washed and then everted to expose the mucosal surface. To obtain surface cells, the everted colons are either scraped gently over the mucosa with a glass slide or incubated for 15 min at 37° C. in Na-citrate buffer containing (mM) 96 NaCl, 27 Na citrate, 0.8 KH$_2$PO$_4$, 5.6 Na$_2$HPO$_4$, and 1.5 D-Glucose, pH 7.4. To obtain isolated crypts, colonic segments are incubated for 15 min at 37° C. in Na-EDTA buffer containing (mM) 96 NaCl, 1.5 KCl, 21 Na EDTA, 55 Sorbitol, 22 Sucrose, and 10 HEPES, pH 7.4 (Method 3). At the end of each incubation, colonic segments are vigorously agitated for 30 sec to release surface cells or individual crypts. Released cells or crypts are immediately mixed with 2 volumes of standard Ringers solution containing (mM) 125 NaCl, 5.0 KCl, 1.0 CaCl$_2$, 1.2 MgSO$_2$, 2.0 NaH$_2$PO4, 5.0 D-Glucose, and 32 HEPES, pH 7.4. Cells are collected by centrifugation (2000 rpm for 5 min in Beckman Coulter Allegra 6R Centrifuge), washed three times in basal Ringers solution, and resuspended in basal Ringers solution. Basal Ringers solution contains the same composition as standard Ringers except that both Ca$^{2+}$ and Mg are reduced to 0.1-0.5 mM.

For isolation of different fractions or zones of crypt cells, a sequential digestion of colonic segments in the Na-EDTA buffer is employed. Following a 15 min incubation in the Na-citrate buffer and removal of surface cells, colons are transferred into the Na-EDTA buffer and incubation at 37° C. for 5 min. Colonic segments are then agitated and removed from the buffer, and the buffer is centrifuged to provide a pellet consisting of the outer one-third of the crypts. Continous incubation of colonic segments with Na-EDTA buffer (5 min, 37° C.) followed by vigorous agitation releases the middle one-third of the crypts. A further 3-5 min incubation with agitation released the inner one-third of the crypts. The released cells are diluted in 2 volumes of ice cold Standard Ringers and collected by centrifugation. Sequential separation of surface cells and the three zones of crypt cells can be validated by measuring alkaline phosphatase activity (measured in a DU® 640B spectrophotometer (Beckman Coulter) according to the manufacturer's instructions (Sigma Diagnostics, Inc., St. Louis, Mo.) using p-nitrophenyl phosphate as substrate. Results are expressed as the increase in absorbance per minute per mg protein at a wavelength of 405 nm).

Net Fluid (Jv) Measurements

The method used for measurements of net fluid movement (Jv, nl/min*mm crypt length) in the isolated perfused colonic crypt has been published in detail in Geibel, J. P. et al. 2001. Gastroenterology 120: 144-150. Jv is calculated as the rate at which the effluent accumulated in the collection pipette and the concentrations of methoxy-[$^3$H]inulin in the perfusate and effluent. Positive Jv values indicate net fluid movement from lumen to bath (absorption), and negative values indicate fluid movement from bath to lumen (secretion). FIG. 1 demonstrates measurement of net Jv (nl/min*mm crypt length), which is made up of two components: a large fluid flux from lumen to bath (the absorptive Basal $^{abs}$Jv) and a small bath to lumen flux of secretory component (in the absence of secretagogues; basal $^{sec}$Jv). Additional of basolateral bumetanide abolishes the $^{sec}$Jv and a "pure" absorptive flux equals $^{net}$Jv=$^{abs}$Jv+$^{sec}$Jv; $^{abs}$Jv is a positive flux and $^{sec}$Jv is a negative flux.

The method described above can be used for mice, rats and for human material.

Measurement of Intracellular $Ca^{2+}$ Responses in Colonocytes

The calcimimetic or calcilytic properties of compounds could also be evaluated using measurements of changes in intracellular $Ca^{2+}$ of isolated colonic cell suspensions using Fluo-3 or Fura-2. Cells are exposed to a solution of either Fluo-3 AM or Fura-2 AM at 5 µM for 20 to 30 min at room temperature to allow uptake and ester hydrolysis. The cells are then washed at 37° C. for about 20 min to remove any extracellular dye that had not been taken up or had desesterified on the extracellular surface of the crypts. Fluorescence measurements (Fluo-3: 480 nm excitation, 520 nm emission, 5 nm bandpass; Fura-2: 340/380 nm excitation, 512 nm emission, 5 nm bandpass) on cells suspensions are performed in a thermostatically regulated 2 ml cuvette maintained at 37° C. with constant stirring in a basal Ringer-solution containing 0.1 mM $Ca^{2+}$. The cumulative intracellular $Ca^{2+}$ response at a given concentration of the calcimimetic or calcilytic is determined.

Short-Circuit Current Measurement in Intestinal Sheets

The calcimimetic or calcilytic properties of compounds could also be evaluated using measurements of short-circuit current in intestinal sheets. Segments of colon or small intestine are removed quickly from rats or mice, or from human surgical specimens. Segments are cut along the mesenteric border into a flat sheet and flushed with ice-cold basal HEPES-Ringer solution containing 0.1 mM Ca and Mg. Either the entire small intestinal layer or a mucosal colonic layer that has the serosa, longitudinal and circular muscular and submucosa layers stripped off are used. The intestinal sheet is mounted between two halves of a modified Ussing chamber and short-circuited by a voltage clamp (VCC MC6; Physiologic Instruments) with correction for solution resistance. The exposure area is 0.3-1.0 $cm^2$. The mucosal and serosal surfaces of the tissue are bathed in reservoirs with 3-5 mL Hepes-Ringer solution, pH 7.4, maintained at 37° C. and continuously bubbled with 100% $O_2$. Tissues are allowed a minimum of 40-minute stabilization and basal recording period before compounds are added to the apical or basolateral side of the epithelium. Responses were recorded continuously and data were acquired via DATAQ™ instruments and were stored in a PC and processed using the program Acqualize™. The Hepes-Ringer solution contains (in mmol/L): NaCl 125; KCl 5; $MgCl_2$ 0.5; HEPES 22, $CaCl_2$ 0.1 or 1.6; glucose 10, pH 7.4. The solution is bubbled with 100% $O_2$. After achieving a stable basal or forskolin-stimulated negative short circuit current, the responses of the current to serosal or mucosal side additions of compounds is monitored.

MTC 6-23 Cell Calcitonin Release

Rat MTC 6-23 cells (clone 6), purchased from ATCC (Manassas, Va.) are maintained in growth media (DMEM high glucose with calcium/15% HIHS) that is replaced every 3 to 4 days. The cultures are passaged weekly at a 1:4 split ratio. Calcium concentration in the formulated growth media is calculated to be 3.2 mM. Cells are incubated in an atmosphere of 90% $O_2$/10% $CO_2$, at 37° C. Prior to the experiment, cells from sub-confluent cultures are aspirated and rinsed once with trypsin solution. The flasks are aspirated again and incubated at room temperature with fresh trypsin solution for 5-10 minutes to detach the cells. The detached cells are suspended at a density of $3.0×10^5$ cells/mL in growth media and seeded at a density of $1.5×10^5$ cells/well (0.5 mL cell suspension) in collagen-coated 48 well plates (Becton Dickinson Labware, Bedford, Mass.). The cells are allowed to adhere for 56 hours post-seeding, after which the growth media was aspirated and replaced with 0.5 mL of assay media (DMEM high glucose without/2% FBS). The cells are then incubated for 16 hours prior to determination of calcium-stimulated calcitonin release. The actual calcium concentration in this media is calculated to be less than 0.07 mM. To measure calcitonin release, 0.35 mL of test agent in assay media is added to each well and incubated for 4 hours prior to determination of calcitonin content in the media. Calcitonin levels are quantified according to the vendor's instructions using a rat calcitonin immunoradiometric assay kit (Immutopics, San Clemente, Calif.).

Inositol Phosphate Assay

The calcimimetic or calcilytic properties of compounds could also be evaluated in a biochemical assay performed on Chinese hamster ovarian (CHO) cells transfected with an expression vector containing cloned CaSR from rat brain [CHO(CaSR)] or not [CHO(WT)] (Ruat M. & Snowman A M., J. Biol. Chem 271, 1996, p 5972). CHO (CaSR) has been shown to stimulate tritiated inositol phosphate ([$^3$H]IP) accumulation upon activation of the CaSR by $Ca^{2+}$ and other divalent cations and by Compound A (N-(3-[2-chlorophenyl]-propyl)-R-■-methyl-3-methoxybenzylamine HCl) (Ruat et al., J. Biol. Chem 271, 1996). Thus, [$^3$H]IP accumulation produced by 10 µM of each CaSR-active compound in the presence of 2 mM extracellular calcium can be measured and compared to the effect produced by 10 mM extracellular calcium, a concentration eliciting maximal CaSR activation (Dauban P. et al., Bioorganic & Medicinal Chemistry Letters, 10, 2000, p 2001). This assay can also be used to evaluate [$^3$H]$IP_3$ accumulation in response to calcimimetic or calcilytic compounds in isolated colonic crypts or dispersed colonocytes (Cheng et al., Gastroenterology 126, 2004, p 148).

Solutions and Chemicals

The HEPES-Ringer solution contained (in mmol/L): NaCl 125; KCl 5; $MgCl_2$ 0.5; HEPES 22, $CaCl_2$ 0.1 or 1.6; glucose 10, pH 7.4. The solution was bubbled with 100% $O_2$. Forskolin, IBMX, and bumetanide were obtained from Sigma Chemical (St Louis, Mo., USA) and stock solutions were prepared in dimethyl sulphoxide (DMSO). Final concentrations of DMSO never exceeded 0.1% (v/v). Preliminary experiments indicated that the vehicle did not alter any baseline electrophysiological parameters.

CTX, STA and Guanylin were formulated in HEPES-Ringer buffer to the desired concentrations as shown in FIG. 2.

EXAMPLE 2

This experiment demonstrates the effect of calcimimetics on fluid secretion.

To assess the functional relevance of the CaSR in the colon epithelial cells, particularly its ability in modulating intestinal fluid movement in diarrheal states, the effect of luminal or basolateral CaSR activation and modulation on Jv was determined in isolated rat colonic crypts in both basal and agents that affect cAMP and cGMP levels.

Figure 2A:
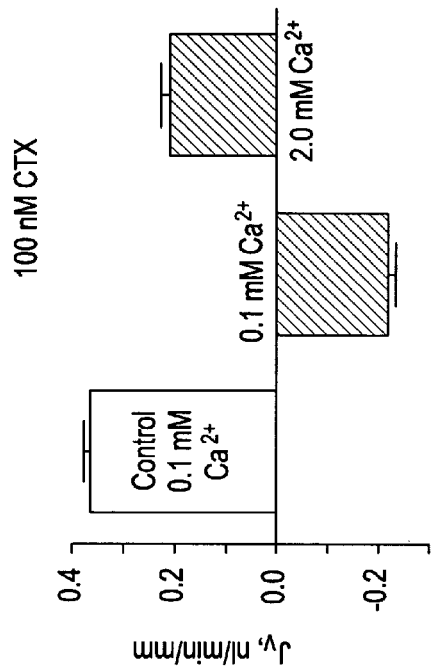
FIG. 2 schematically represents that luminal or bath $Ca^{2+}$ abrogates toxin-induced fluid secretion in in vitro perfused rat colonic crypts.
Figure 2B:
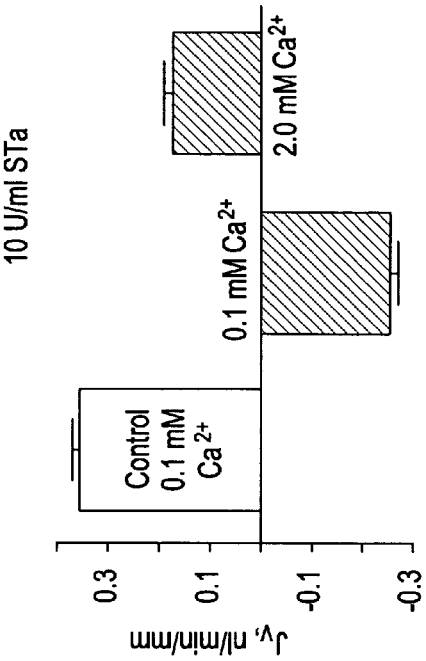

FIGS. 2A and 2B summarize the changes in Jv in perfused colonic crypts in the absence and presence of agents that induce cAMP production (e.g., forskolin, cholera toxin), before and after raising extracellular calcium from 0.1 mM to 2 mM in the bath or luminal perfusate. In the absence of forskolin or cholera toxin, the mean Jv values indicate net fluid absorption (A and B, open bars). Exposure to forskolin or cholera toxin at 0.1 mM Ca induced net fluid secretion (A and B, solid bars). Raising $Ca^{2+}$ from 0.1 mM to 2 mM in either the bath or lumen perfusate reversed net fluid secretion induced by forskolin or cholera toxin, resulting in net fluid absorption (A and B solid bars).

Figure 2C:
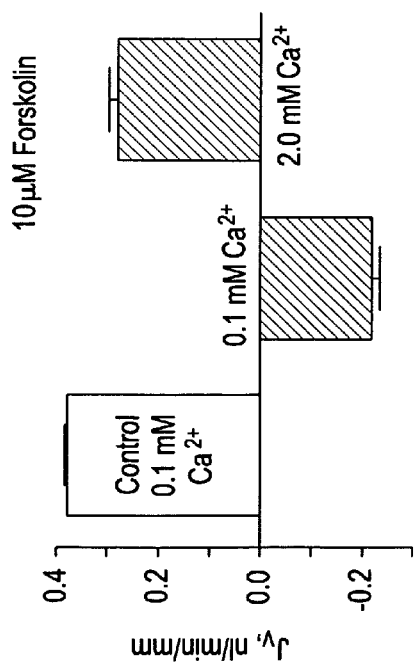
Figure 2D:
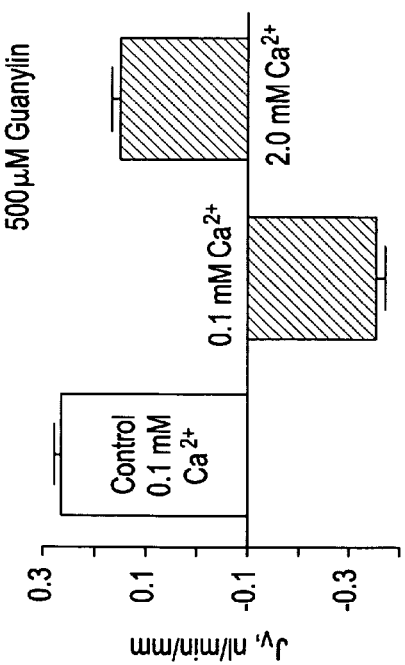
Figure 8A:
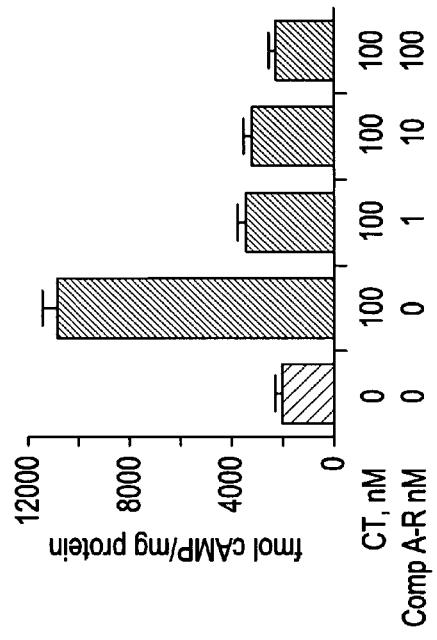
FIG. 8 demonstrates that toxin-induced cyclic AMP or GMP production is attenuated by the calcimimetic in a dose-dependent manner.
Figure 8B:
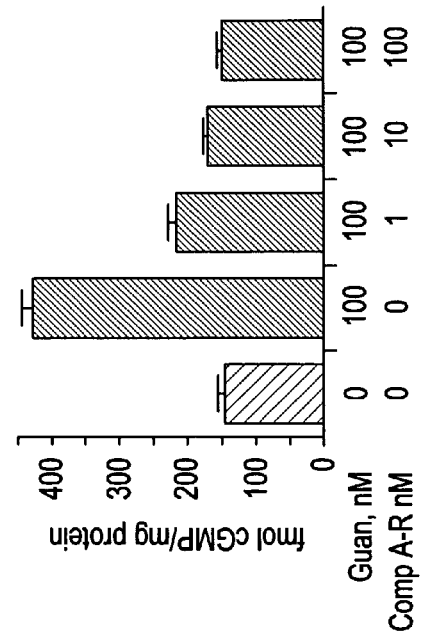
Figure 8C:
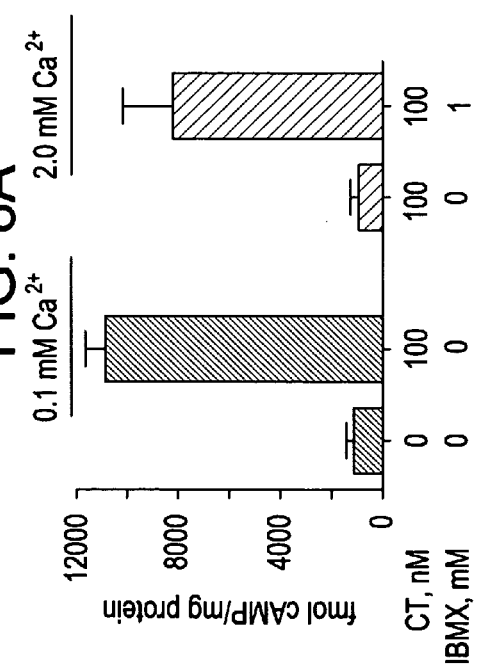
Figure 8D:
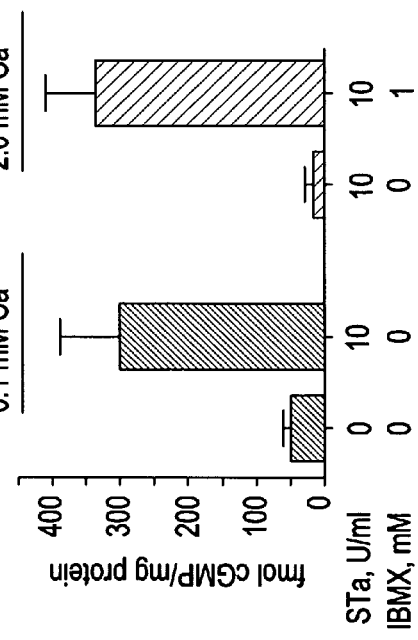

FIGS. 2C and 2D summarize the changes in Jv in perfused colonic crypts in the absence and presence of agents that induce cGMP production (e.g., Guanylin, STa), before and after raising extracellular calcium from 0.1 mM to 2 mM in the bath or luminal perfusate. In the absence of Guanylin or STa, the mean Jv values indicate net fluid absorption (C and D, open bars). Exposure to Guanylin or STa at 0.1 mM Ca induced net fluid secretion (A and B, solid bars). Raising $Ca^{2+}$ from 0.1 mM to 2 mM in either the bath or lumen perfusate reversed net fluid secretion induced by Guanylin or STa, resulting in net fluid absorption (C and D, solid bars).

FIG. 3 (A-G) illustrates that Compound A in a dose-dependent manner attenuates forskolin-induced net fluid secretion in the presence of 0.1 mM $Ca^{2+}$ in the bath. Solid bars (Panels A-G) indicate the net fluid absorption in the absence of forskolin and Compound A. Open bars indicate the net fluid secretion in the presence of forskolin (10 µM). Hatched bars (Panels A-G) indicate that Compound A in a dose-dependent manner attenuates bath net fluid secretion with the $EC_{50}$ of 5.1 pM (FIG. 3, panel H).

FIG. 4 (A-G) illustrates that R568 in a dose-dependent manner attenuates forskolin-induced net fluid secretion in the presence of 0.1 mM $Ca^{2+}$ in the lumen. Solid bars (Panels A-G) indicate the net fluid absorption in the absence of forskolin and Compound A, R-stereoisomer. Open bars indicate the net fluid secretion in the presence of forskolin (10 µM). Hatched bars (Panels A-G) indicate that Compound A in a dose-dependent manner attenuates luminal net fluid secretion with the $EC_{50}$ of 23.4 pM (FIG. 4, panel H).

FIG. 5 (A-G) illustrates that S568 in a dose-dependent manner attenuates forskolin-induced net fluid secretion in the presence of 0.1 mM $Ca^{2+}$ in the bath. Solid bars (Panels A-G) indicate the net fluid absorption in the absence of forskolin and Compound A, S-stereoisomer. Open bars indicate the net fluid secretion in the presence of forskolin (10 µM). Hatched bars (Panels A-G) indicate that Compound A, S-stereoisomer, in a dose-dependent manner attenuates bath net fluid secretion with the $EC_{50}$ of 619 pM (FIG. 5, panel H).

FIG. 6 (A-G) illustrates that Compound A, S-stereoisomer, in a dose-dependent manner attenuates forskolin-induced net fluid secretion in the presence of 0.1 mM $Ca^{2+}$ in the lumen. Solid bars (Panels A-G) indicate the net fluid absorption in the absence of forskolin and Compound A. Open bars indicate the net fluid secretion in the presence of forskolin (10 µM). Hatched bars (Panels A-G) indicate that Compound A, S-stereoisomer in a dose-dependent manner attenuates luminal net fluid secretion with the $EC_{50}$ of 756 pM (FIG. 6, panel H).

EXAMPLE 3

This example demonstrates the effect of $Ca^{2+}$ and calcimimetics on secretagogue-stimulated cyclic nucleotide accumulation. Cyclic nucleotide accumulation was measured using the following method. Briefly, colonic crypt cell suspensions were incubated at 37° C. with 1 µM Forskolin (Sigma, Saint Louis, Mo.) for 15 min, 1 µM guanylin and 10 µM STa for 45 min in the presence or absence of 1 mM IBMX (3-Isobutyl-1-Methylxanthine) (Sigma, Saint Louis, Mo.). The crypts were exposed to a Hepes buffer containing either low $Ca^{2+}$ (0.1 mM $Ca^{2+}$) or a high $Ca^{2+}$ (2 mM) or $Gd^{3+}$ (250 µM). After addition of agonists and/or IBMX (0 or 1 mM), the reactions were terminated at the end of each time point by addition of 2 ml of ice-cold pure (100%) ethanol to 1 ml of crypt cell suspensions, resulting in a final suspension volume of 66% (v/v) ethanol. The suspensions were allowed to settle, and then the supernatant was drawn off into test tubes. The remaining precipitate was washed with ice cold 66% (v/v) ethanol and added to appropriate test tubes, which are labeled based on $Ca^{2+}$ and IBMX concentrations. The extracts were centrifuged at 2000 rpm for 15 min at 40° C. and the supernatant was transferred into fresh tubes. The extracts were then lyophilized under 65° C. vacuum centrifugation. Cyclic AMP and cyclic GMP (in femtomoles per milligram of cell protein) were measured using a commercially available enzyme immunoassay kit (Amersham, Buckingham, England).

FIG. 7 (A, B) illustrates that forskolin (A) and cholera toxin (B) induce cAMP production when the CaSR is inactive (solid bars, 0.1 mM $Ca^{2+}$). Activation of the CaSR by 2.0 mM of extracellular $Ca^{2+}$ attenuates the forskolin or cholera toxin induced cyclic AMP production. Addition of isobutyl-1-methyl-xanthine (IBMX), a PDE inhibitor, reverses this effect.

FIG. 7 (C, D) illustrates that Guanylin (C) and STa (D) induce cGMP production when the CaSR is inactive (solid bars, 0.1 mM $Ca^{2+}$). Activation of the CaSR by 2.0 mM of extracellular $Ca^{2+}$ attenuates the Guanylin or STa induced cyclic GMP production. Addition of IBMX (1 mM) reverses this effect.

FIG. 8 (A) illustrates that cholera toxin induce cyclic AMP production when the CasR is inactive (solid bars, 0.1 mM $Ca^{2+}$). Activation of the CasR by 2.0 mM of extracellular $Ca^{2+}$ attenuates cholera toxin induced cyclic AMP production. Addition of IBMX reverses this effect.

FIG. 8 (B) illustrates that STa induces cyclic GMP production when the CasR is inactive (solid bars, 0.1 mM $Ca^{2+}$). Activation of the CasR by 2.0 mM of extracellular $Ca^{2+}$ attenuates STa induced cyclic GMP production. Addition of IBMX reverses this effect.

FIG. 8 (C) illustrates that cholera toxin induces cyclic AMP production when the CasR is inactive (solid bars, 0.1 mM $Ca^{2+}$). Addition of the calcimimetic Compound A (R-stereoisomer) attenuates cyclic AMP in a doze-dependent manner (solid bars) to that of control levels (open bar).

FIG. 8 (D) illustrates that Guanylin induces cyclic GMP production when the CasR is inactive (solid bars, 0.1 mM $Ca^{2+}$). Addition of the calcimimetic attenuates cyclic GMP in a dose-dependent manner (solid bars) to that of control levels (open bar).

EXAMPLE 4

FIGS. 9A, 9B and 9C demonstrate that Compound A (R-stereoisomer) has no effect on net Jv in absence and presence of forskolin and the PLC inhibitor U73122 in rat clonic crypts. In the forskolin absence, the mean Jv values indicate net fluid absorption (A, B and C, open bars). Exposure to forskolin and the phosphatidylinositol-phospholipase C (PLC) inhibitor (U73122, 10 μM) in the presence of 0.1 mM calcium induced net fluid secretion (A, B and C solid bars). Addition of Compound A to the lumen or bath had no significant effect on reversing net fluid secretion (A and B, solid bars), indicating a role for CasR-mediated activation of PI-PLC. Addition of Compound A to both luminal and bath did not completely reverse net fluid secretion (C solid bars).

EXAMPLE 5

This example demonstrates the effect of the calcimimetic on P38-related TNF-alpha toxicity in mice.

Female BALB/c mice (18-20 g) were obtained from Charles River Laboratories and allowed to acclimatize for at least two weeks prior to study. rHu-TNF-alpha was obtained from Amgen Protein Sciences. Mice were dosed orally with 2-(((2S)-2-amino-3-phenylpropyl)amino)-3-methyl-5-(2-naphthalenyl)-6-(4-pyridinyl)-4(3H)-pyrimidinone (Compound C) at 10 mg/kg (200 μl/mouse) one hour prior to challenge with TNF-alpha (10 μg/mouse, IV). Compound B (N-((6-(methyloxy)-4'-(trifluoromethyl)-1,1'-biphenyl-3-yl)methyl)-1-phenylethanamine) was administered SC at the same time as Compound C at doses of 1, 3, 10, or 30 mg/kg. Five of 10 mice from each treatment group were sacrificed at 3 hrs following administration of TNF-alpha for determination of small intestinal fluid accumulation. The full length of the small intestine was carefully dissected, the proximal and distal ends were clamped and the intact small intestine was removed from the abdominal cavity. The intestinal luminal fluid contents were drained into a conical tube and the volume was measured. The remaining 5 mice from each group were monitored for survival.

Figure 10:
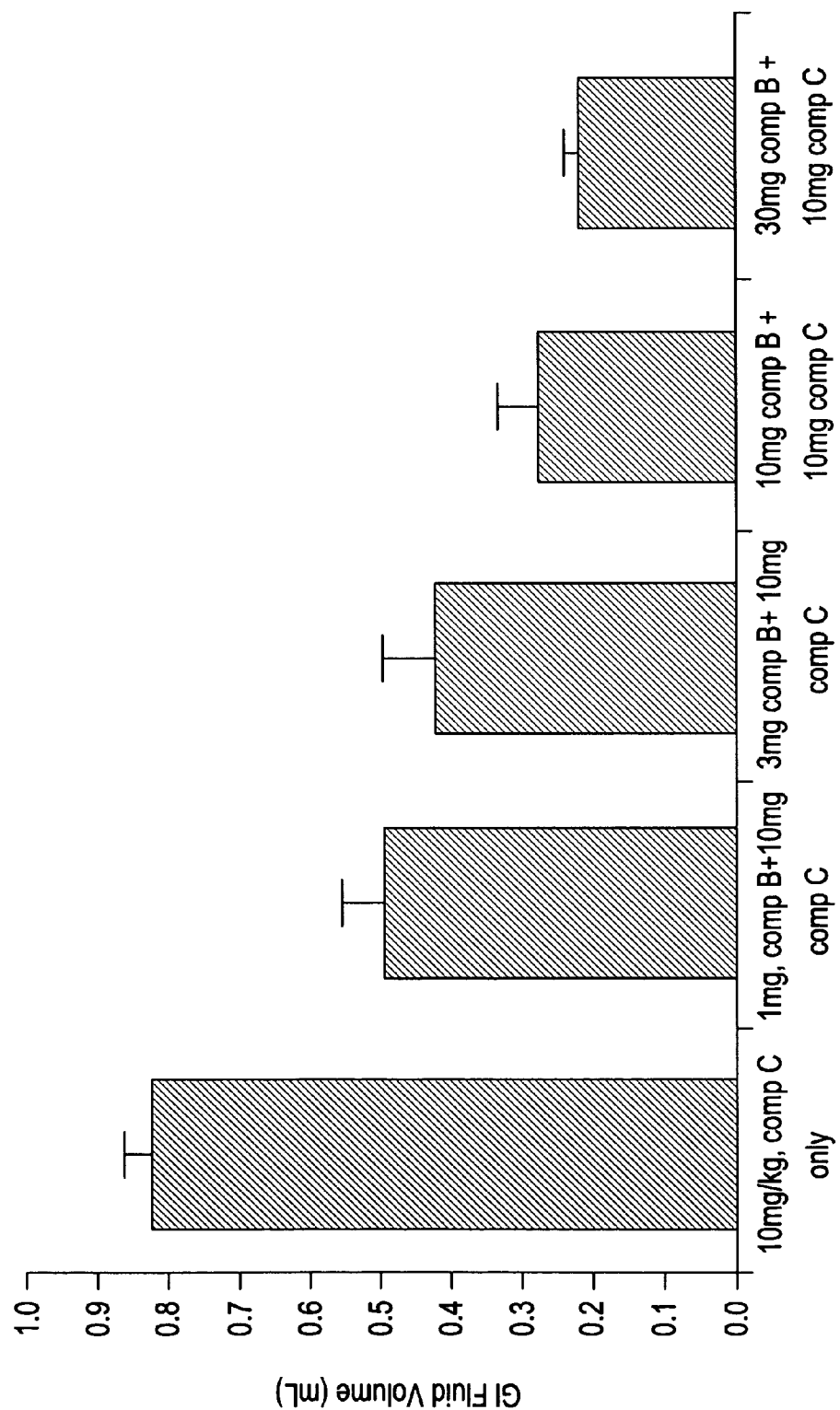
FIG. 10 demonstrates the effect of the calcimimetic treatment on P38-related TNF-alpha toxicity in mice.

FIG. 10 demonstrates that treatment with Compound B caused a dose-dependent reduction in the volume of fluid accumulating in the small intestine. Mice that were allowed to survive beyond 3 hours showed 100% mortality as expected after the co-administration of Compound C and human TNF-alpha. Treatment with Compound B at 10 mg/kg fully protected against lethality (Table 5). The lower dose of Compound B partially protected against lethality.

TABLE 5

| | Mortality data | | | |
|---|---|---|---|---|
| # of mice for | Mortality | | | Dose of Compound B |
| Observation | 3 hrs | 6 hrs | 24 hrs | mg/kg |
| 5 | 5/5 moribund | 2/5 dead | 5/5 dead | 0 |
| 5 | 5/5 OK | 5/5 moribund | 5/5 dead | 1 |
| 5 | 5/5 OK | 5/5 OK | 3/5 dead 2/5 moribund | 3 |
| 5 | 5/5 OK | 5/5 OK | 5/5 OK | 10 |

EXAMPLE 6

This experiment demonstrates the lack of effect of calcium and a calcimimetic on secretagogue-stimulated net fluid secretion in CaSR null mice.

Double Casr- and Gcm2-deficient mice were created as described in Qisheng Tu et al. J. Clin Invest. 111:1029-1037, 2003. Deletion of the Casr gene results in early postnatal mortality from the toxic effects of unregulated release of parathyroid hormone (PTH) from parathyroid chief cells as well as from the pathological effects of the consequent hypercalcemia, Ho, C. et al. Nature Genetics 11, 389-394, 1995. Glial cells missing 2 (Gcm2) is a regulatory gene critical for parathyroid gland development. Deletion of Gcm2 results in mice having no parathyroid glands. Gunther, T. et al. Nature 406, 199-203, 2000. However, these $Gcm2^{-/-}$ mice exhibit a low circulating level of PTH probably emanating from the thymus sufficient to maintain skeletal integrity, and this source of PTH is not regulated by the CaSR (Gunther, T. et al. Nature 406, 199-203, 2000; Tu et al. J. Clin. Invest. 111 1029-1037, 2003). Thus, deletion of Gcm2 eliminates the early mortality in Casr-null mice.

To assess the functional relevance of the CaSR in colon epithelial cells, particularly its ability in modulating intestinal fluid movement in diarrheal states, the colonic crypts were removed from wild type mice ($Casr^{+/+}:Gcm2^{+/+}$ normal) and from mice in which the CaSR has been deleted ($Casr^{-/-}:Gcm2^{-/-}$).

FIG. 11 summarizes the changes in net Jv in perfused colonic crypts from $Casr^{+/+}:Gcm2^{+/+}$ and $Casr^{-/-}:Gcm2^{-/-}$ mice in the absence and presence of agents that either induce cGMP (Guanylin) or cAMP (CTX) production before and after raising extracellular calcium from 0.1 mM to 2 mM in the bath.

The mean Jv values indicate net fluid absorption (FIG. 11, A and C) in perfused colonic crypts from either $Casr^{+/+}:Gcm2^{+/+}$ or $Casr^{-/-}:Gcm^{-/-}$ mice in the absence of toxins and with a calcium concentration of 0.1 mM. Exposure to Guanylin or CTX at 0.1 mM calcium induced net fluid secretion (FIG. 11, A and C; CTX, open bars, Guanylin, sold bars). Raising extracellular calcium concentration from 0.1 mM to 2 mM reversed net fluid secretion induced by Guanylin and CTX in the colonic crypts from $Casr^{+/+}:Gcm2^{+/+}$ mice (FIG. 11A), but did not in the crypts from $Casr^{-/-}: Gcm2^{-/-}$ (FIG. 11C).

Figure 11A:
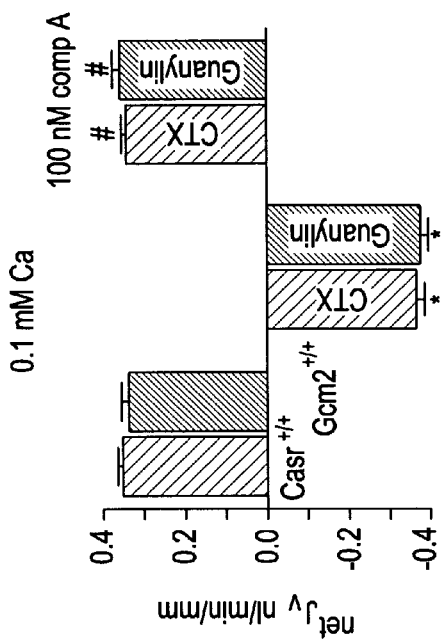
FIG. 11 demonstrates the absence of effects of $Ca^{2+}$ or the calcimimetic Compound A on secretagogue-stimulated net fluid secretion in CaSR null mice.
Figure 11B:
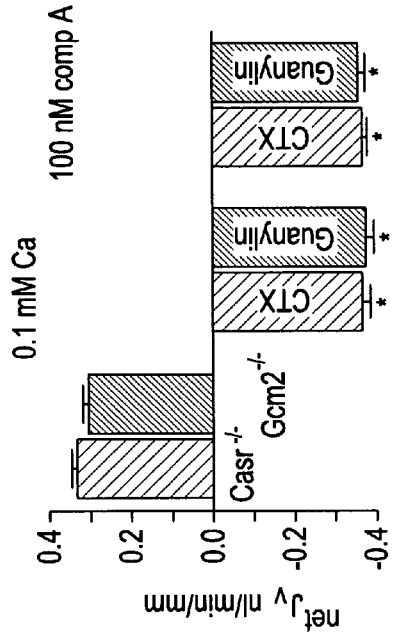
Figure 11C:
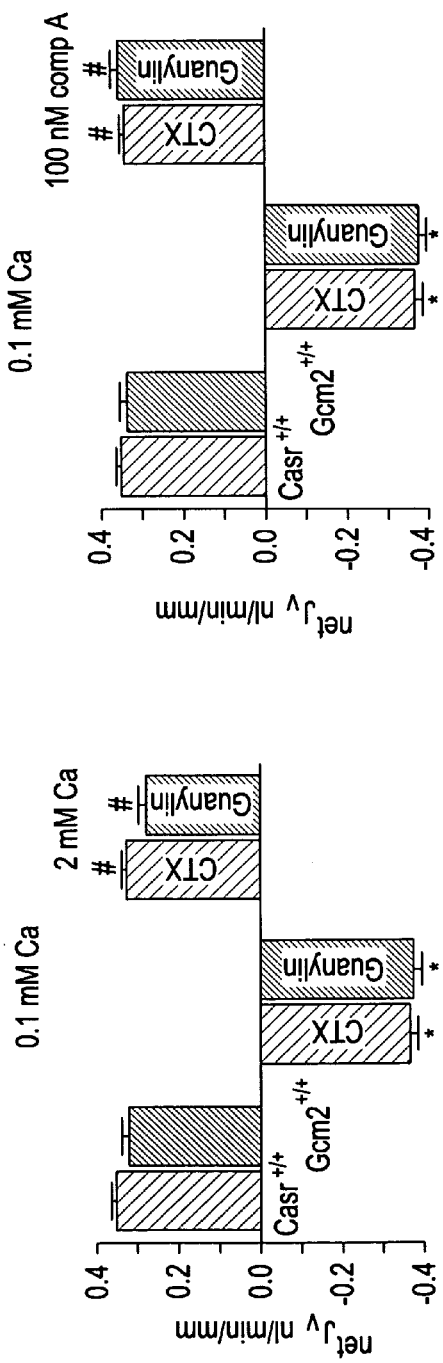
Figure 11D:
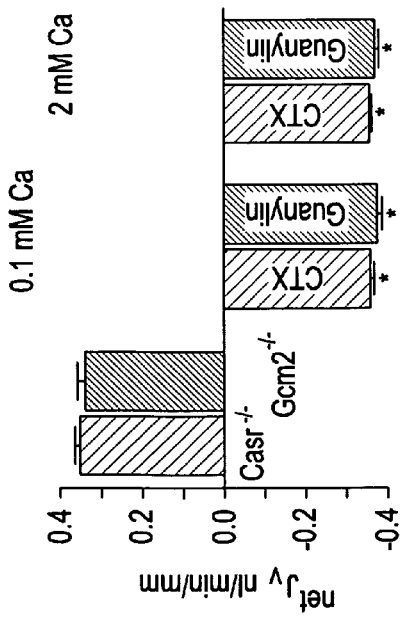

Addition of Compound A (R-stereoisomer), 100 nM, did not reverse net fluid secretion induced by Guanylin (solid bars) and CTX (open bars) in the colonic crypts from $Casr^{-/-}:Gcm2^{-/-}$ mice in the presence of 0.1 mM calcium (FIG. 11D), whereas addition of this calcimimetic effectively reversed net fluid secretion induced by these agents in the colonic crypts from $Casr^{+/+}:Gcm2^{+/+}$ mice in the presence of 0.1 mM calcium (FIG. 11B). In FIG. 11, values are Mean±SEM. Asterisk, P<0.001 as compared to no secretagogue: #, P<0.01 compared to secretagogue without CaSR agonist.

EXAMPLE 7

This Example demonstrates that either extracellular calcium or Compound A reverse secretagogue-induced secretion of chloride ions from basolateral (blood-interstitial) side to crypt lumen in rat colonic crypts.

Fluid secretion into the lumen of colonic crypts depends on movement of chloride ions ($Cl^-$) across the luminal plasma membrane through the cystic fibrosis transmembrane conductance regulator chloride channels, CFTR. Neves, S. R. et al. Science 296, 1636-1639, 2002. Secretagogue-induced increases in cellular accumulation of cAMP or cGMP enhances PKA and PKG phosphorylation processes (Golin-Bisello, F. et al. Am. J. Cell Physiol. 289, C708-C716, 2005; Neves et al.), respectively, which drives translocation of activated CFTR channels to the luminal plasma membrane. Equally critical for transepithelial $Cl^-$ transport during secretagogue-stimulated fluid secretion is increased $Cl^-$ entry into cells from basolateral fluid via the bumetanide-sensitive Na-K-2Cl cotransporter (NKCC1). Adult mice lacking NKCC1 exhibit impaired secretory responses to cAMP and STa (Flagella, M. et al. J. Biol. Chem. 274, 26946-26955, 1999).

$Cl^-$ Measurements. Cell $Cl^-$ influx measurements (Egan, M. E. et al. Nat. Med. 8, 485-492, 2002) were performed on isolated superfused colonic crypts on glass coverslips coated with cell-tak (Cell-Tak™, BD bioscience, Bedford, Mass.) and loaded with 20 mM MQAE [(N-6-methoxyquinolyl) acetoethyl ester; Molecular Probes]. After dye loading, crypts were incubated in a $Cl^-$ free HEPES buffer until stable high baseline fluorescence intensity was achieved. Rates of cell $Cl^-$ influx were monitored as rates of reductions in arbitrary MQAE fluorescent units ($\Delta$AFU/min; Ex: 346 nm; EM: 460 nm).

Figure 12A:
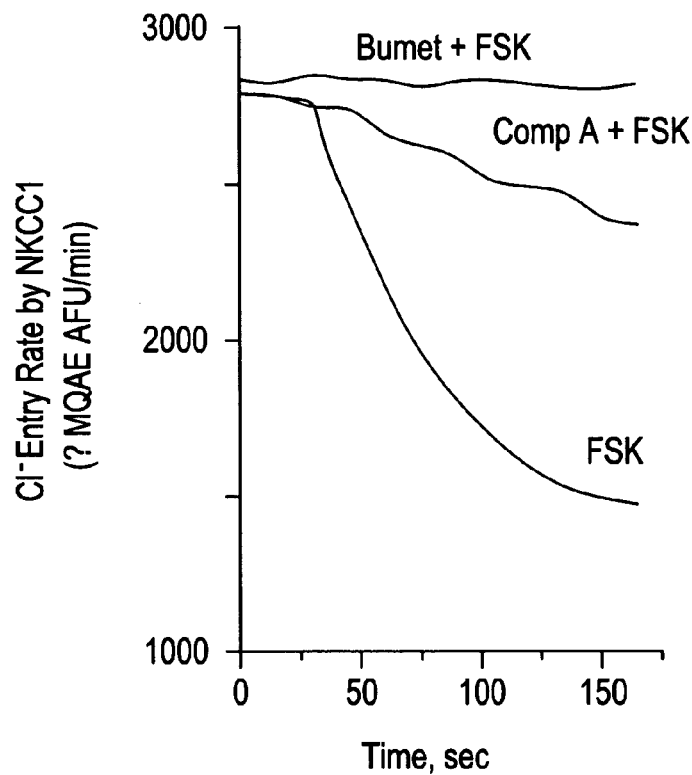
FIG. 12 demonstrates that in rat perfused colonic crypts, basolateral addition of forskolin in the presence of 0.1 mM calcium stimulates basolateral $Cl^-$ entry into colonic crypt cells.
Figure 12B:
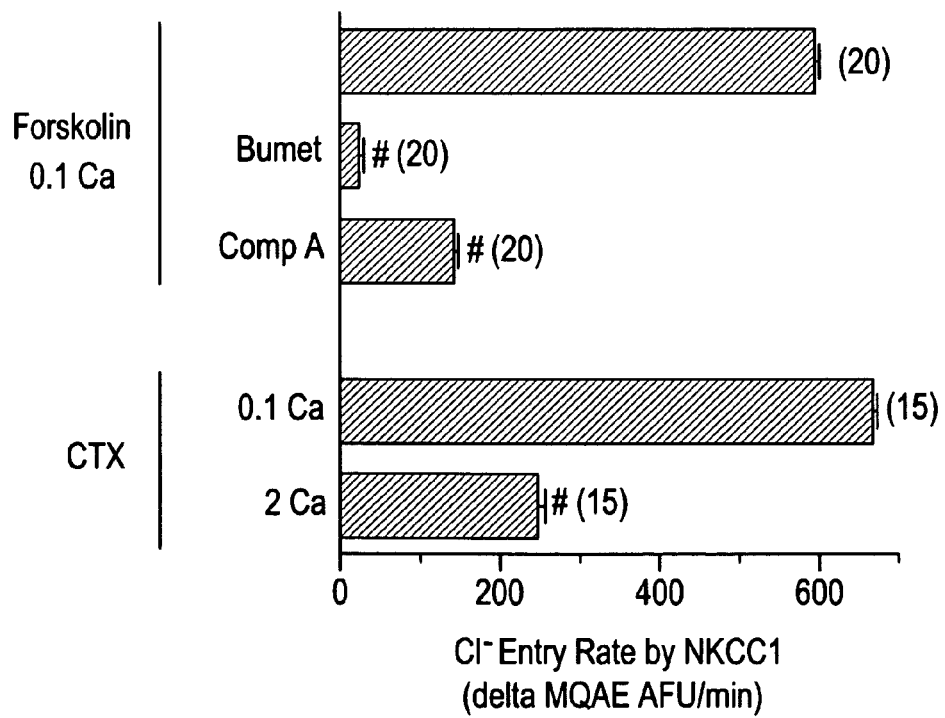

Effect of $Ca^{2+}$ and calcimimetics on Forskolin-stimulated basolateral $Cl^-$ entry into colonic crypt cells. Results presented in FIG. 12 (A and B) demonstrate that in rat perfused colonic crypts, basolateral addition of forskolin in the presence of 0.1 mM calcium stimulates basolateral $Cl^-$ entry into colonic crypt cells (rise in cell $Cl^-$ monitored by the fall in MQAE fluorescence). In rat perfused colonic crypts, basolateral addition of 100 µM bumetanide, which inhibits $Cl^-$ influx through the NKCC1 cotransporter, abolished forskolin-stimulated increase in cell $Cl^-$ via basolateral $Cl^-$ entry into colonic crypt cells. Addition of the calcimimetic Compound A (100 nM) to the basolateral fluid also significantly reduced the rate of forskolin-stimulated $Cl^-$ entry. Extracellular $Ca^{2+}$ at concentration of 0.1 mM did not abolish CTX-stimulated basolateral $Cl^-$ entry into colonic crypt cells (FIG. 12B). Increasing the concentration of calcium from 0.1 to 2 mM inhibited $Cl^-$ entry via NKCC1 in the presence of CTX (FIG. 12B). Values in B are Mean±SEM. Asterisk, P<0.01 as compared to no secretagogue, #, P<0.01 compared to secretagogue without inhibitor or CaSR agonist. The number in parenthesis is the number of crypts studied. Calcium (Ca) concentrations are in millimolar.

These studies demonstrate that activation of the CaSR inhibits NKCC1 activity, a critical component of fluid secretory mechanism.

EXAMPLE 8

This Example demonstrates that either extracellular calcium or Compound A reverses secretagogue-induced inhibition of fluid absorption in rat colonic crypts.

Figure 13A:
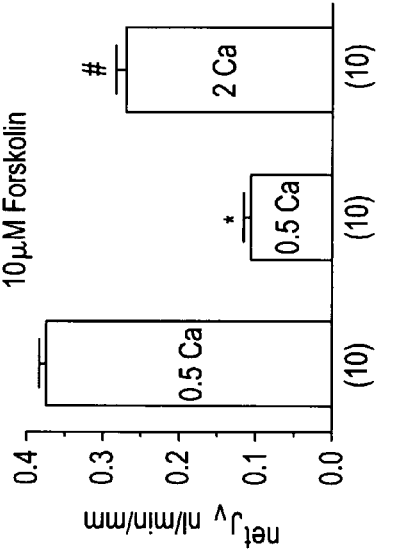
FIG. 13 demonstrates that either extracellular calcium or Compound A reverses secretagogue-induced inhibition of fluid absorption in rat colonic crypts.
Figure 13B:
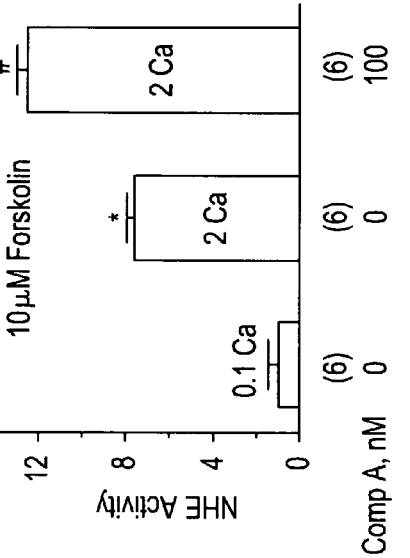
Figure 13C:
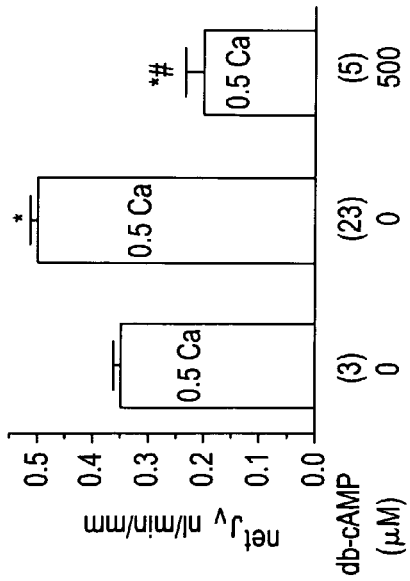
Figure 13D:
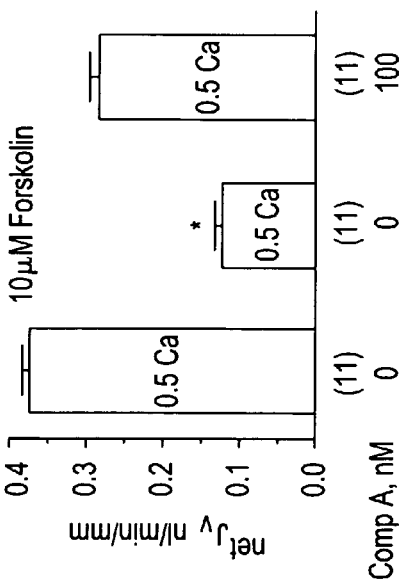

Cyclic nucleotide-dependent fluid loss in secretory diarrheas occurs through reduction in absorptive, and increases in secretory, processes. Lucas, M. L. J. Appl. Microbiol. 90, 7-26, 2001; Golin-Bisello, F. et al. Am. J. Cell. Physiol. 289, C708-C716, 2005. Colonic epithelial crypts provide a model for understanding intestinal fluid transport as they simultaneously absorb and secrete fluid with the direction of net fluid movement ($^{net}Jv$) depending on the relative magnitudes of these two processes. A major component of fluid absorption in the colon is mediated by parallel $Na^+/H^+$ (sodium-hydrogen exchanger, NHE) and $Cl^-/HCO_3^-$ exchange located at the apical plasma membranes. Kunzelman, K. et al. Physiol. Rev. 82, 245-289, 2002; Donowith, M. et al. Annu. Rev. Physiol. 48, 135-150, 1986. Cyclic nucleotides reduce this $Na^+$-dependent fluid absorption by inhibiting NHE activity. In the absence of secretagogues, addition of bumetanide to the basolateral bath of perfused crypts increased the positive or absorptive $^{net}Jv$ due to inhibition of a small remaining fluid secretion (FIG. 13A, second bar). This basal fluid was likely due to the low levels of cell cyclic nucleotides that remain even in the absence of secretagogues. Thus in the presence of bumetanide, $^{net}Jv$ measurements represent the absorptive component of fluid transport. FIG. 13A demonstrates that this absorptive fluid movement was substantially reduced by addition of the cell-permeable dibutyryl-cAMP (db-cyclic AMP). In FIG. 13B fluid secretion was inhibited by addition of bumetanide to the basolateral bath plus 5-nitro-2-(3-phenylpropylamino)-benzoic acid (NPPB, a $Cl^-$ channel inhibitor) to the luminal perfusate of perfused crypts. FIG. 13B demonstrates that this absorptive fluid movement is inhibited by forskolin. The inhibition of fluid absorption by cyclic AMP or the cyclic AMP-generating secretagogue, forskolin, would importantly contribute to secretagogue-induced diarrheas. Either increasing the concentration of extracellular $Ca^{2+}$ to 2 mM (FIG. 13B) and/or addition of Compound A (FIG. 13C) to the basolateral bath (in the presence of 0.5 mM calcium) significantly abrogated the cAMP-mediated reduction in fluid absorption. To examine if this latter effect of CaSR agonists on fluid absorption resulted from enhanced apical NHE activity, the effects of $Ca^{2+}$ on $Na^+$-dependent proton extrusion from colonocytes were assessed in the presence of forskolin. NHE activity was increased 8-fold by raising basolateral bath $Ca^{2+}$ from 0.1 to 2 mM, and addition of Compound A to the 2 mM $Ca^{2+}$-containing bath resulted in a further increase in NHE activity to 12-fold (FIG. 13D). Cell acid loading was accomplished by exposure to $NH_4Cl$ and $Na^+$-dependent cell pH recovery following removal of $NH_4Cl$ was assessed as an index of $Na^+/H^+$ activity. Singh et al. Proc. Natl. Acad. Sci. U.S. 92 11573-11577, 1995. Values in A-D are Mean±SEM. Asterisk, P<0.01 as compared to no secretagogue, #, P<0.01 compared to secretagogue without inhibitor or CaSR agonist. The number in parenthesis is the number of crypts studied. Calcium (Ca) concentrations are in millimolar.

EXAMPLE 9

This Example demonstrates the effect of the calcimimetic on cholera toxin-induced gastrointestinal fluid accumulation in mice.

Female BALB/c mice (18-20 g) were obtained from Charles River Laboratories and allowed to acclimatize for at least two weeks prior to study. Cholera toxin was obtained from Biomol (purified cholera toxin from *Vibrio cholerae*, azide free). Mice (n=5/group) were fasted overnight prior to oral administration of cholera toxin at 50 µg/mouse. Mice were administered vehicle or Compound B orally at 30 or 100 mg/kg one hour prior to cholera toxin administration (50

µg/mouse, orally). Another group of mice received Compound B at 20 mg/kg intravenously (tail vein) one hour prior to cholera toxin (50 µg/mouse orally). Mice were sacrificed 6 hours following cholera toxin administration for determination of gastrointestinal fluid accumulation. The full length of the small intestine was carefully dissected, the proximal and distal ends were clamped and the intact small intestine was removed from the abdominal cavity. The intestinal luminal fluid contents were drained into a conical tube and the volume measured.

Figure 14:
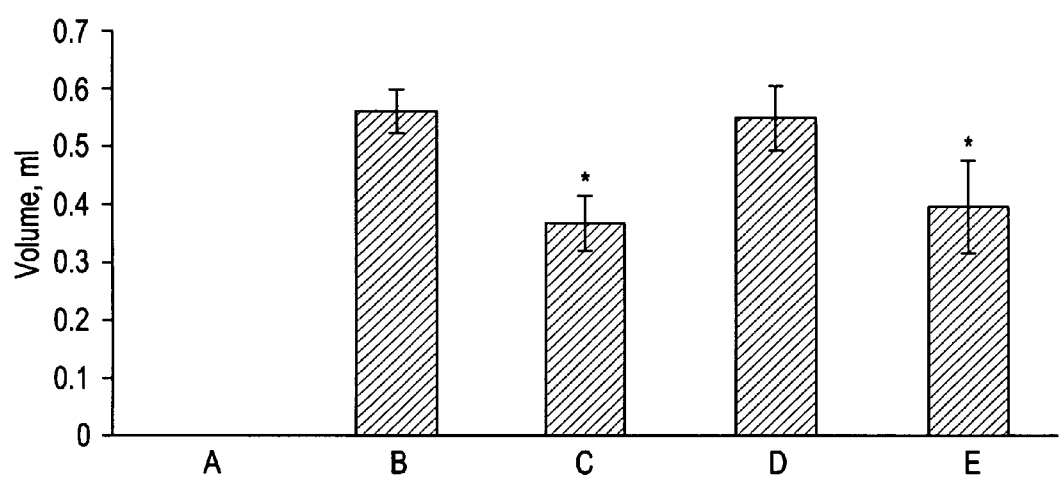
FIG. 14 illustrates that treatment with Compound B [N-((6-(methyloxy)-4'-(trifluoromethyl)-1,1'-biphenyl-3-yl)methyl)-1-phenylethanamine] mediated a statistically significant reduction of cholera toxin induced gastrointestinal fluid accumulation, at doses of 100 mg/kg orally, or 20 mg/kg intravenously.

FIG. 14 illustrates that treatment with Compound B resulted in a statistically significant reduction of cholera toxin-induced gastrointestinal fluid accumulation, at doses of 100 mg/kg orally, or 20 mg/kg intravenously. Panel A, control; panel B, vehicle; panel C. 20 mg/kg IV; panel D, 30 mg/kg PO; panel E, 100 mg/kg PO; *p<0.05 vs. vehicle control by Bonferroni/Dunn analysis.

EXAMPLE 10

This Example demonstrates that the calcimimetics act via the direct pathway in either proximal or distal colon in the perfused crypt model.

In normal rodents and humans the enteric nervous system (mainly the submucosal plexus) liberates agents that regulate fluid secretion (Cooke, H. J. (1998) *News Physiol. Sci.* 13:269274; Field, M. (2003) *J Clin. Invest.* 111:931-943). There is evidence from in vivo studies that the enteric nervous system plays a role in enterotoxin (e.g., cholera toxin and STa)—induced fluid secretion in intestine (Field, M. supra). This has been determined by the use of tetrodotoxin (TTX), a neural poison and a potent sodium channel blocker that inhibits neuronal action potential propagation. It has been suggested that TTX reverses cholera toxin-induced fluid secretion in the intestine. Studies have shown that the effect of enterotoxins causing secretory diarrheas may be at least in part via activation of the enteric nervous system (ENS) through activation of enterochromaffin cells (EC) (Burleigh et al. (1997) *Dig Dis Sci,* 42: 1964-1968; Field M. supra). Further, the CaSR is not only expressed in intestinal epithelial cells, but also in the enteric nervous system, such as the myenteric plexus in smooth muscle and the submucosal plexus (Chattopadhyay, N et al. (1998) *Am. J. Physiol.* 274: G122-G130). This would suggest that the presence of the CaSR in the enteric nervous system may play a role in the modulation of fluid secretion.

Fluid secretion stimulated by secretagogues (e.g., forskolin, cholera toxin, STa) can be mediated by either (or both) direct activation of intestinal epithelial cells (direct pathway) and indirect activation of intestinal cells via the EC-ENS (indirect pathway). Secretagogues that directly activate intestinal cells capable of chloride secretion are not affected by TTX while the effect of secretagogues that active the EC-ENS indirect secretion pathway is abolished by this neurotoxin. Therefore, TTX can be used to distinguish whether a secretagogue is working via the direct or indirect pathways. The inability of TTX to abolish or diminish fluid secretion is evidence for the absence of participation of the ENS in fluid secretion. The isolated crypt preparation lacks an intact enterochromaffin cell-enteric nervous system but expresses the CaSR on crypt epithelial cells. Thus, the isolated crypt preparation was used to test whether TTX influences the calcimimetics' ability to reverse forskolin-induced net fluid secretion via direct activation of crypt epithelial cells.

Direct Enterocyte Pathway

To study the direct effect of calcimimetics on forskolin-stimulated fluid secretion, the standard perfused crypt protocol was used as described in Geibel et al. (2006) Nat'l Acad. Sci. Proc. 103(25): 9390-9397. All data were analyzed as described in Geibel et al. Briefly, proximal and distal colon crypts were hand dissected from intestinal segments of adult Sprague-Dawley rats and then mounted between concentric glass pipettes to allow independent perfusion of the crypt lumen and blood-interstitial surface. The activity of [$^3$H] Inulin, a non-absorbable volume marker, was used to quantify fluid secretion or absorption by the perfused crypt.

Figure 15A:
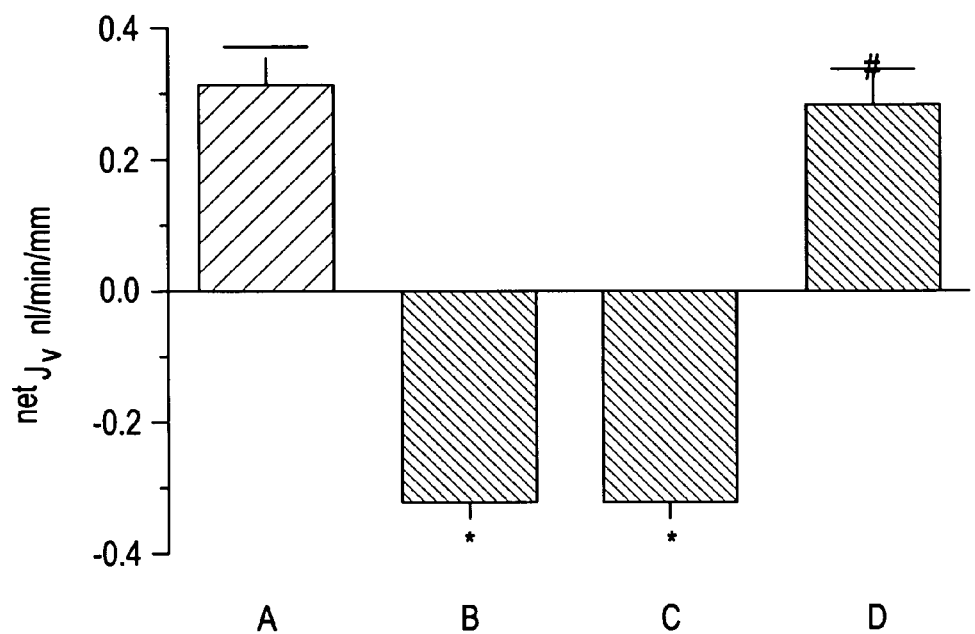
FIG. 15 demonstrates that TTX has no effect on the magnitude of forskolin-induced fluid secretion or the ability of Compound A to reverse the forskolin-stimulated increase in fluid absorption in both the proximal and distal colon in the perfused crypt model.
Figure 15B:
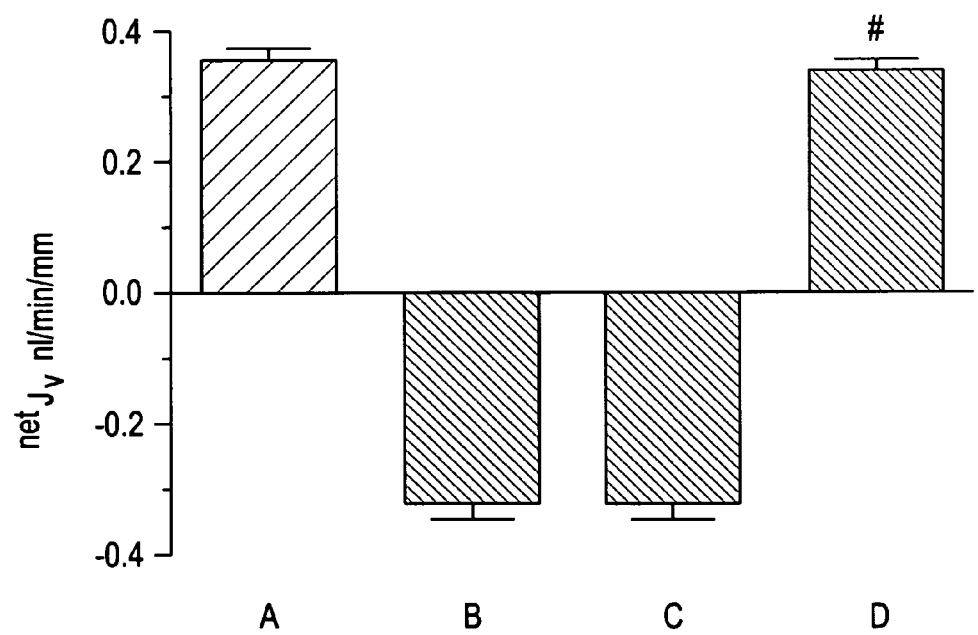
Figure 16A:
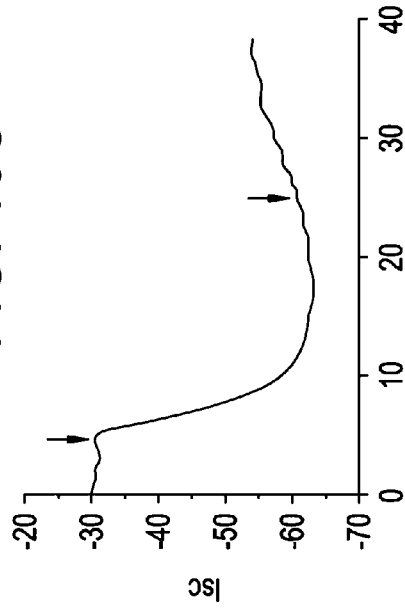
FIG. 16 illustrates that the ability of Compound A to reverse the forskolin-stimulated increase in the short-circuit current ($I_{sc}$) is abolished by TTX in 6-7 week old rats in the Ussing chamber model.
Figure 16B:
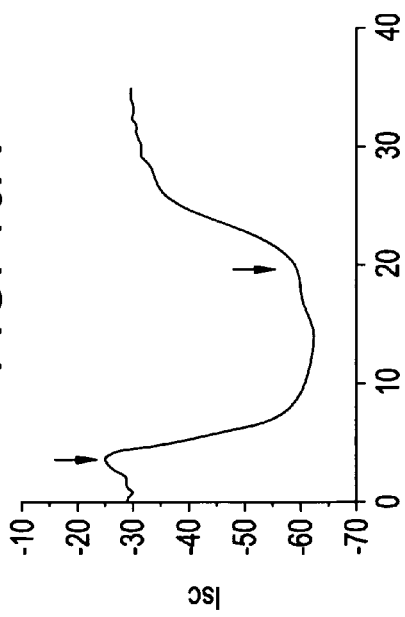
Figure 16C:
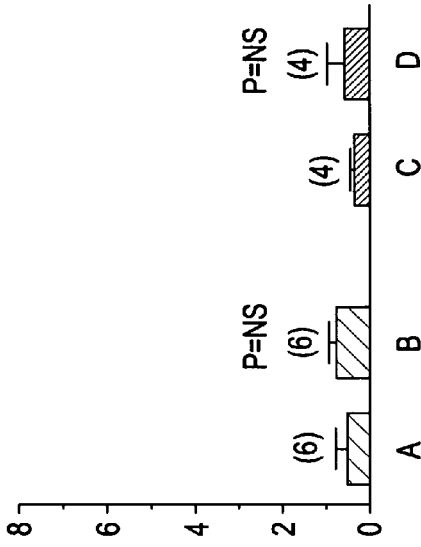
Figure 16D:
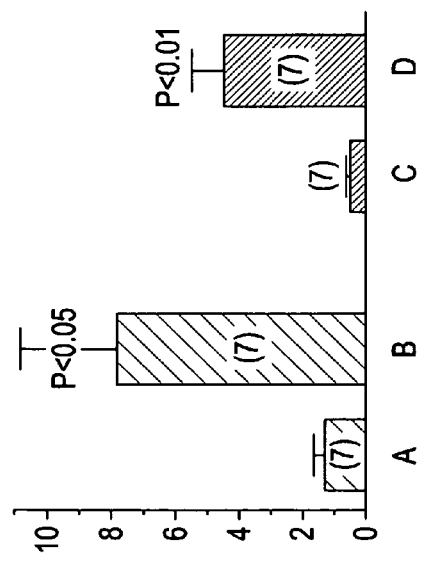

FIG. 15 demonstrates that 2 µM TTX has no effect on the magnitude of forskolin-induced fluid secretion or the ability of the calcimimetic (Compound A, 100 nM) to reverse the forskolin-stimulated increase in fluid absorption in both the proximal (panel A) and distal colon (panel B) in the perfused crypt model. In both panels, bars A: control (0.1 mM $Ca^{2+}$ perfusate and bath Ringer solution), bars B: 0.1 mM $Ca^{2+}$+ 500 nM forskolin; bars C: 0.1 mM $Ca^{2+}$+500 nM forskolin+2 µM TTX; bars D: 0.1 mM $Ca^{2+}$+500 nM forskolin+2 µM TTX+100 nM Compound A. Asterisk, P<0.01 as compared to no secretagogue, #, P<0.01 compared to secretagogue without inhibitor or CaSR agonist.

In the absence of forskolin the mean Jv values indicate net fluid absorption in both proximal (A open bar; 0.31±0.02 nL/min/mm) and distal (B open bar; 0.36±0.01 nL/min/mm) colonic crypts. Exposure to forskolin (bars B, both panels) induced net fluid secretion in both proximal and distal colonic crypts (−0.32±0.02 nL/min/mm, proximal; −0.33±0.01 nL/min/mm, distal). The addition of TTX did not change the ability of forskolin to induce a net fluid secretion in both proximal and distal colon (both panels, bars C). Bars D, both panels indicate that the calcimimetic Compound A attenuated forskolin-induced net fluid secretion and that the presence of TTX had no influence on this pharmacological response in both proximal and distal colon. These data are consistent with the lack of an intact enterochromaffin cell-enteric nervous system in isolated crypts and that calcimimetics act via the direct pathway in either proximal or distal colon in the perfused crypt model.

EXAMPLE 11

This experiment demonstrates that calcimimetics can abrogate fluid secretion and that this effect is mediated via the enterochromaffin cell-enteric nervous system (EC-ENS), as demonstrated using the Ussing chamber model. It is further demonstrated that calcimimetics are effective in both proximal and distal colon, as well as in both infant and adult animals.

Enterochromaffin Cell-enteric Nervous System (EC-ENS) and the Ussing Chamber Model.

As stated in Example 10, the effect of enterotoxins causing secretory diarrheas may be at least in part via activation of the enteric nervous system (ENS) through activation of enterochromaffin cells (EC) and that the presence of the CaSR in the enteric nervous system may play a role in the modulation of fluid secretion. Enterotoxins activate intestinal enterochromaffin cells to release 5-hydroxytryptamine (5-HT) which stimulates the enteric nervous system via 5-HT1b receptors. The enteric nervous system sends signals to enterocytes to secrete fluid via vasoactive intestinal peptide and other factors (secretagogues). The application of enterotoxins stimulate increases in cAMP and cGMP in enterochromaffin cells and this triggers these cells to release neuron-active peptides which mediates the increase in intestinal fluid secretion (Cooke; Field, supra). This EC-ENS mediated mechanism of diarrhea (fluid secretion) can be inhibited by the neurotoxin, tetrodotoxin (TTX), which acts on the ENS to block the release of secretagogues.

Intestinal fluid secretion induced by enterotoxins and the effect of calcimimetics on the fluid balance was studied using an in vitro model, the Ussing chamber. This model involves the EC-ENS pathway and is described in detail in Li, H. et al. (2004) *J. Cyst. Fibrosis* 3: 123-126. Briefly, proximal or distal colon segments are isolated from suckling (2-3 weeks of age) or young adult (6-7 weeks of age) Sprague-Dawley rats and placed in ice-cold buffer. Small pieces of full thickness colon are cut and mounted in a plexiglass Ussing chamber with bicarbonate-free Ringer's solution on both the mucosal and serosal chambers. The serosal chamber is gassed with 100% $O_2$ and both serosal and mucosal fluids warmed to 37° C. When open circuit transepithelial voltage is stable the tissue is short circuited and short circuit current ($I_{sc}$; $\mu A/cm^2$) monitored. The short-circuit current ($I_{sc}$) is defined as the charge flow per time when the tissue is short-circuited.

FIG. 16 demonstrates that the ability of calcimimetics to reverse the forskolin-stimulated increase in the short-circuit current ($I_{sc}$) is abolished by TTX in young adult rats. The experiment was done using 6-7 week old Sprague-Dawley rats. Ussing Chamber data were reported either as total $I_{sc}$ ($\mu A/cm^2$) or as the rate of change in $I_{sc}$ ($\mu A/cm^2$ min) before (control) versus after addition of Compound A. Rates were determined by linear regression. For all experiments, a representative $I_{sc}$ current vs. time tracing from the distal colon is also shown.

In panel A, the addition of 500 nM of forskolin (5 min, first arrow) to the bath in the absence of TTX induced an increase in the negative $I_{sc}$ in proximal colon indicating the forskolin-induced fluid secretion. This was reversed by the bath application of 10 µM of Compound A (20 min, second arrow). The results presented in panel C indicate that in the presence of 2 µM of TTX, the addition of 10 µM of Compound A (25 min, second arrow) had virtually no effect on the forskolin-induced $I_{sc}$, in contrast to the decrease in Isc by Compound A in the absence of TTX (panel A). Panels B and D summarize the rate of change in $I_{sc}$ ($\mu A/cm^2$ min), Y axis, before (control) versus after addition of Compound A in proximal and distal colon. Panel B, no TTX: A, proximal colon, control (before adding Compound A); B, proximal colon, after addition of 10 µM Compound A; C, distal colon, control (before adding Compound A); D, distal colon, after addition of 10 µM Compound A. Panel D, 2 µM TTX: A, proximal colon, control (before adding Compound A); B, proximal colon, after addition of 10 µM Compound A; C, distal colon, control (before adding Compound A); D, distal colon, after addition of 10 µM Compound A.

FIG. 17 demonstrates that the ability of calcimimetics to reverse the forskolin-stimulated increase in the short-circuit current ($I_{sc}$) is abolished by TTX in infant animals. The experiment was conducted as described before using 2-3 week old Sprague-Dawley rats. Similar to the experiment illustrated in FIG. 16, the addition of 500 nM of forskolin (FIG. 17, panel A; 5 min, first arrow) to the bath in the absence of TTX induced a increase in the negative $I_{sc}$ in distal colon indicating the forskolin-induced fluid secretion. This was reversed by the bath application of 10 µM of Compound A (18 min, second arrow). The results presented in panel C indicate that in the presence of 2 µM of TTX, the addition of 10 µM of Compound A (22 min, second arrow) had virtually no effect on the forskolin-induced $I_{sc}$, in contrast to the decrease in Isc by Compound A in the absence of TTX (panel A). Panels B and D summarize the rate of change in $I_{sc}$ ($\mu A/cm^2$ min), Y axis, before (control) versus after addition of Compound A in proximal and distal colon. Panel B, no TTX: A, proximal colon, control; B, proximal colon, 10 µM Compound A; C, distal colon, control; D, distal colon, 10 µM Compound A. Panel D, 2 µM TTX: A, proximal colon, control; B, proximal colon, 10 µM Compound A; C, distal colon, control; D, distal colon, 10 µM Compound A.

This demonstrates that calcimimetics can abrogate fluid secretion in both proximal and distal colon from in infant or adult animals and that this effect of calcimimetics is mediated via the enterochromaffin cell-enteric nervous system (EC-ENS).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating diarrhea in a subject comprising administering an effective amount of a pharmaceutical composition comprising at least one calcimimetic compound together with a pharmaceutically acceptable carrier to the subject wherein the calcimimetic compound is N-(3-[2-chlorophenyl]-propyl)-R-α-methyl-3-methoxybenzylamine; N-((6-(methyloxy)-4'-(trifluoromethyl)-1,1'-biphenyl-3-yl)methyl)-1-phenylethanamine or cinacalcet HCl.

2. The method of claim 1, wherein the diarrhea is an osmotic, secretory, exudative or a rapid transit diarrhea.

3. The method of claim 1, wherein the diarrhea is an acute or chronic diarrhea.

4. The method of claim 1, wherein the diarrhea is a traveler's diarrhea.

5. The method of claim 1, wherein the diarrhea is caused by *E. coli, Shigella, Salmonella, Campylobacter jejuni, Vibrio cholerae*, cholera toxin (CTX); *El Tor, Giardiasis, Entamoeba hislolyca, cryptosporidium parvum*; Norwalk viruses, Rotaviruses, Adenoviruses, Caliciviruses, Astroviruses or Enteroviruses.

6. The method of claim 1, wherein the diarrhea is cyclic AMP-mediated.

7. The method of claim 1, wherein the diarrhea is associated with or resulting from a rise in cyclic GMP.

8. The method of claim 1, wherein the diarrhea is caused by antibiotics, anti inflammatory medicine, caffeine, steroids, drugs or laxatives.

9. The method of claim 1, wherein the diarrhea is caused by malabsorption or maldigestion.

10. The method of claim 9, wherein the diarrhea is caused by lactase deficiency.

11. The method of claim 1, wherein the diarrhea is caused by short bowel syndrome.

12. The method of claim 1, wherein the diarrhea is associated with a gastrointestinal surgical procedure.

13. The method of claim 1, wherein the diarrhea is associated with an abdominal surgical procedure.

14. The method of claim 1, wherein the diarrhea is associated with chemotherapy, radiation treatment, inflammation or toxic traumatic injury.

15. The method of claim 1, wherein the subject is human.

* * * * *